(12) United States Patent
Schiff

(10) Patent No.: US 6,713,055 B2
(45) Date of Patent: Mar. 30, 2004

(54) GLYCOSYLTRANSFERASE VECTORS FOR TREATING CANCER

(75) Inventor: J. Michael Schiff, Menlo Park, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/994,427

(22) Filed: Nov. 26, 2001

(65) Prior Publication Data

US 2002/0128221 A1 Sep. 12, 2002

Related U.S. Application Data

(60) Provisional application No. 60/253,395, filed on Nov. 27, 2000.

(51) Int. Cl.$^7$ .................. A01N 63/00; C12N 15/00; C12N 15/63; C12N 5/00; C07H 21/04

(52) U.S. Cl. .................. 424/93.21; 536/23.5; 536/24.1; 435/320.1; 435/455; 435/325

(58) Field of Search ............................. 424/93.2, 93.21; 514/44; 435/325, 320.1, 455; 536/23.5, 24.1

(56) References Cited

U.S. PATENT DOCUMENTS

| | | | |
|---|---|---|---|
| 5,068,191 A | 11/1991 | Clausen et al. | 435/193 |
| 5,326,857 A | 7/1994 | Yamamoto et al. | 536/23.2 |
| 5,631,236 A | 5/1997 | Woo et al. | 514/44 |
| 5,698,443 A | 12/1997 | Henderson et al. | 435/320.1 |
| 5,728,379 A | 3/1998 | Martuza et al. | 424/93.2 |
| 5,801,029 A | 9/1998 | McCormick | 435/172.3 |
| 5,821,117 A | 10/1998 | Sandrin et al. | 435/320.1 |
| 5,846,945 A | 12/1998 | McCormick | 514/44 |
| 5,849,991 A | 12/1998 | d'Apice et al. | 800/2 |
| 5,869,035 A * | 2/1999 | Link, Jr. et al. | 424/93.7 |
| 5,871,726 A | 2/1999 | Henderson et al. | 424/93.2 |
| 5,997,859 A | 12/1999 | Barber et al. | 424/93.2 |
| 5,998,205 A | 12/1999 | Hallenbeck et al. | 435/325 |
| 6,096,718 A | 8/2000 | Weitzman et al. | 514/44 |
| 6,133,029 A | 10/2000 | Gruber et al. | 435/366 |
| 6,183,993 B1 * | 2/2001 | Boyce et al. | 435/69.7 |
| 6,340,461 B1 * | 1/2002 | Terman | 424/193.1 |

FOREIGN PATENT DOCUMENTS

| | | |
|---|---|---|
| EP | 0 702 084 | 12/1999 |
| GB | 2 321 642 | 8/1998 |
| WO | WO 97/04748 | 2/1997 |
| WO | WO 9738109 * | 10/1997 |
| WO | WO 98/14593 | 4/1998 |
| WO | WO 98/39466 | 9/1998 |
| WO | WO 99/08692 | 2/1999 |
| WO | WO 99/27113 | 6/1999 |
| WO | WO 99/33998 | 7/1999 |
| WO | WO 00/46355 | 8/2000 |
| WO | WO 01/88096 | 11/2001 |

OTHER PUBLICATIONS

Anderson; Human gene therapy, 1998, Nature, vol. 392: 25–30.*

Nishikawa et.al.; Nonviral Vectors in the New Millennium Delivery Barriers in Gene Transfer, 2001, Human Gene Therapy 12: 861–870.*

Balicki et.al.; Reviews in Molecular Medicine, 2002, Medicine 81: 69–86.*

Rozenberg et.al.; Alternative gene delivery, 2001, S.T.P. Pharma Sciences 11:21–30.*

Chester et.al.; The ABO Blood Group Gene: A Locus of Considerable Genetic Diversity, 2001, Transfusion Medicine Reviews, vol. 15: 177–200.*

Marionneau et.al. ABH and Lewis histro–blood group antigens, a model for the meaning of oligosaccharide diversity in the face of a changing world, 2001, Biochimie 83: 565–573.*

Pan et.al.; A novel tumor–specific gene therapy for bladder cancer, 1999, Medical Hypotheses 53: 130–135.*

Alemany, et al., Complementary adenoviral vectors for oncolysis, Cancer Gene Therapy 6:21 (1999).

Andrews, et al., Inhibition of Proliferation and Induction of Differentiation of Pluripotent Human Embryonal Carcinoma Cells By Osteogenic Protein–1 (Or Bone Morphogenetic Protein–7), Laboratory Investigation 71:243 (1994).

Costa, et al., Comparative analysis of three genetic modificaitons designed to inhibit human serun–mediated cytolysis, Xenotransplantation 6:6 (1999).

Costache, et al., Evolution of Fucosyltransferase Genes in Vretebrates, J Biol Chem 272:29721 (1997).

Galili, et al., "Man, Apes, and Old World Monkeys Differ From Other Mammals in the Expression of Alpha–Galactosyl Epitopes on Nucleated Cells", J. Biol. Chem., 263(33):17755–17762 (1988).

Galili, et al., "Gene Sequences Suggest Inactivation of Alpha–1,3–Galactosyltransferase in Catarrihines After the Divergence of Apes From Monkeys", Proc. Natl. Acad. Sci. USA, 88:7401–7404 (1991).

Galili, et al., Evolution and pathophysiology of the human natural anti–α–galactosyl IgG (anti–Gal) antibody, Springer Semin Immunopathol 15:155 (1993).

(List continued on next page.)

Primary Examiner—Shin-Lin Chen
(74) Attorney, Agent, or Firm—David J. Earp

(57) ABSTRACT

This disclosure provides a system for specifically killing cancer cells which can be used in the course of human therapy. Vectors of the invention comprise an encoding sequence for a glycosyltransferase, under control of a tumor or tissue specific transcriptional control element, such as the promoter for telomerase reverse transcriptase. Exemplary glycosyltransferases are the A or B transferase enzymes, which cause the cancer cells to express ABO histo blood group allotypes against which humans have naturally occurring antibody. This provides for ongoing surveillance for newly emerging cells with a malignant phenotype.

10 Claims, 6 Drawing Sheets

OTHER PUBLICATIONS

Galili, et al., "Natural–Gal Antibody as a Universal Augmenter of Autologous Tumor Vaccine Immunogenicity", Immunology Today, 18:201 (1997).

Gorelik, et al., "Alterations of Cell Surface Carbohydrates and Inhibition of Metastatic Property of Murine Melanomas by Alpha 1,3 Galactosyltransferase Gene Transfection", Cancer Res., 55:4168–4173 (1995).

Gu, et al., Tumor–specific Transgene expression from the Human Telomerase Reverse Transcriptase Promoer Enables Targeting of the Terapeutic Effects of the *Bax* Gene to Cancers, Cancer Res 60:5359 (2000).

α1,3Galactosyltransferase: A Target for in vivo Genetic Manipulation in Xenotransplantation, Immunological Reviews No. 141 (1994).

Henion, et al., Defining the minimal size of catalytically active primate α1,3 galactosyltrasferase: structure—function studies on the recombinant truncated enzyme, Glycobiology 4:193 (1994).

Horikawa, et al., Cloning and Characterization of the Promoter Region of *Human Telomerase Reverse Transcriptase* Gene, Cancer Research 59:826 (1999).

Joziasse, et al., "Characterization of an α1–3–Galactosyltransferase Homologue on Human Chromosome 12 That is Organized as a Processed Pseudogene", J. Biol. Chem., 266(11):6991–6998 (1991).

Joziasse, et al., Xenotransplantation: the importance of the Galα1,3Gal epitope in hyperacute vascular rejection, Biochimica et Biophysica Acta 1455:403 (1999).

Koike, et al., Direct gene replacement of the mouse α(1,3)–galactosyltransferase gene with human α(1,2)fucosyltransferase gene: Converting α–galactosyl epitopes into H antigens, Xenotransplantation 4:147 (1997).

Koga, et al., A Novel Telomerase–Specific Gen Therapy: Gene Transferof Caspase–8 Utilizing the Human Telomerase Catalytic Subunit Gene Promoter, Human Gene Therapy 11:1397 (2000).

Koga, et al., FADD Gene Therapy Using the Human Telomerse Catalytic Subunit (hTERT) Gene Promoter to Restrict Induction of Apoptosis in Tumors In Vitro and In Vivo, Anticancer Research 21:1937 (2001).

Larsen, et al., Frameshift and Nonsense Mutations in a Human Genomic Sequence Homologous to a Murine UDP–Gal:β–D–Gal(1,4)–D–GlcNAc α(1,3)–Galactosyltransferase cDNA, J Biol Chem 12:7055 (1990).

McKenzie, et al., Distribution of the major xenoantigen (gen(α1–3)gal) for pig to human xenografts, Transplant Immunology 2:81 (1994).

Osman, et al., Switching Amino–terminal cytoplasmic Domains of a α(1,2)Fucosyltrnsferase and α(1,3)Galactosyltransferase Alters the Expression of H Substance and Galα(1,3)Gal, J Biol Chem 271:33105 (1996).

Rollins, et al., "Retroviral Vector Producer Cell Killing in Human Serum is Mediated by Natural Antibody and Complement: Strategies for Evading the Humoral Immune Response", Human Gene Terapy, 7:619–626 (1996).

Romans, et al., Monogamous Bivalency of IgG Antibodies—I. Deficiency of Branched ABHI–Active Oligosaccharide Chains, et al., J Immunology 124–2807 (1980).

Sandrin, et al., Transgenic Approaches for the Reduction in Expression of GALα(1,3)GAL for Xenotransplantation, Frontiers in Bioscience 2:1 (1997).

Strokan, et al., Characterisation of human natural anti–sheep xenoantibodies, Xenotransplantation 5:111 (1998).

Takeuchi, et al., Sensitization of cells and retroviruses to human serum by (α1–3) galactosyltransferase, Nature 379:85 (1996).

Walther, et al., Therapeutic Genes for Cancer Gene Therapy, Mol Biol 13:21 (1999).

Xu, et al., Feeder–free growth of undifferentiated human embryonic stem cells, Nature Biotechnology 19:971 (2001).

* cited by examiner

Figure 3(A)

```
Marmoset α1,3GT      MNVKGKVILSMLVVSTVIVVFWEYINSPEGSFLWIYHSKNPEV-DDSSAQKDWWFPGWFNNGIHNYQQEE
human pseudogene
sheep                .....................H.....LF..NP.R....SGG..I..G....R......---.-...
Bovine               .....................H.....LF..NP.R....-GG..I..G..L.R......---.-H..
Pig                  .....R.V....L....M.........LF...Q......--G....RG....S.....T.S.-H..
Mouse                ..........L..I....V......V.RI------------...-GENRW........S..K..T.S.-..D Consensus α1,3GT     ......................................................................
Humanized α1,3GT     ......................................................................

hu B transferase     .AEVLRTLAGKPKCHALRPMILFL.MLV---------------------LVL.GYGVLSPRSLMPGSL
hu A transferase     .AEVLRTLAGKPKCHALRPMILFL.MLV---------------------LVL.GYGVLSPRSLMPGSL Marmoset α1,3GT      EDTDK-EKGREEEQKKEDDTTELRLWDWFNPKKRPEVMTVTQWKAPVVWEGTYNKAILENYYAKQKITVG
human pseudogene
sheep                DEDVDE..EQRK.D.-----SK.K.S.....F.....V.M.D............R.V.DD..........
Bovine               DGDINE..-----RN..E-SK.K.S.....F.....V.M.K............R.V.D...........
Pig                  ..AIGN..-----R...NRG..P.V.....E.....V.I.R............R.V.D...........
Mouse                NVEGRR..-----GRNG.RIE.PQ........N..D.L...P....I......DT.L..K...T..L...

Consensus α1,3GT     ......................................V.M.P....I.......R.V.D..........
Humanized α1,3GT     .......................................................................

hu B transferase     .RGFCMAVREPDHLQRVSLPRMVYPQPKVLTPC.KD.LV..P.L..I.....F.ID..NEQFRL.NT.I.
hu A transferase     .RGFCMAVREPDHLQRVSLPRMVYPQPKVLTPC.KD.LV..P.L..I.....F.ID..NEQFRL.NT.I.

Marmoset α1,3GT      LTVFAIGRYIEHYLEEFVTSANRYFMVGHKVIFYVMVDDVSKAPFIELGPLRSFKVFEVKPEKRWQDISM
human pseudogene         ..ND......I................I........L.........H...M..............
sheep                .....V..........L....KH.....R...........RM.L...................R....V..
Bovine               .....V..........L....KH.....P....I......RM.L...................KI.........
Pig                  .....V.........LI...T...........I....I.RM.L.....................I.S.........
Mouse                .....V.K.......D.LE..DM......R.......I..T.RM.VVH.N..H.LQ...IRS.........

Consensus α1,3GT     .....V.K..........L........R....I......RM.L..............I.S......V..
Humanized α1,3GT     ..........D......L..........I..........................................

hu B transferase     ......KK.VA-F.KL.LET.EKH.....R.HY..FT.QPAAV.RVT..TG.QLS.L..GAY.....V..
hu A transferase     ......KK.VA-F.KL.LET.EKH.....R.HY..FT.QLAAV.RVT..TG.QLS.L..RAY.....V..
```

Figure 3(B)

```
Marmoset α1,3GT      MRMKTIGEHILAHIQHEVDFLFCMDVDQVFQDHFGVETLGQSVAQLQAWWYKADPDDFTYERRKESAAYI
human pseudogene     ....IT..........................................*.R.....Y...*..W....G..
sheep                V.........V....R.................E.......E..............E.............
Bovine               ..........V..............K.......E..............N.....................
Pig                  ..............................NN.........................H..E........
Mouse                ...............................N........L............S.EK......EL.....

Consensus α1,3GT     ...............................N........................E.............
Humanized α1,3GT     ....IT..................................................G..

hu B transferase     R..EM.SDFCERRFLS...Y.V.V...ME.R..V...I.TPLFGT.HPSF.GSSREA......PQ.Q...
hu A transferase     R..EM.SDFCERRFLS...Y.V.V...ME.R..V...I.TPLFGT.HPGF.GSSREA......PQ.Q...

Marmoset α1,3GT      PFGQGDFYYHAAIFGGTPIQVLNITQECFKGILLDKKNDIEAEWHDESHLNKYFLLNKPSKILSPEYCWD
human pseudogene     ...*.........S..................K........................LK....
sheep                ...E............T..............K........Q.................T..........
Bovine               ...E............T..............K........Q.................T..........
Pig                  ................T..............Q..E.......................T..........
Mouse                ...E............THI..L.R.......Q...H....Q..............F...T..........

Consensus α1,3GT     ...E............T..............Q..........................T..........
Humanized α1,3GT     .....................................................................

hu B transferase     .KDE.....MG.F...SVQE.QRL.RA.HQAMMV.QA.G...V...........L.RH..T.V.....L..
hu A transferase     .KDE.....LGGF...SVQE.QRL.RA.HQAMMV.QA.G...V...........L.RH..T.V.....L..

Marmoset α1,3GT      YHIGLPSDIKTVKLSWQTKEYNLVRKNV
human pseudogene     .............*..........N..
sheep                ......A...L..M........V..N..
Bovine               ......A...L..M........V..N..
Pig                  ....MSV..RI..IA..K.......N.I
Mouse                .Q........S..VA..........N..

Consensus α1,3GT     .........................N..
Humanized α1,3GT     ............................

hu B transferase     QQLLGWPAVLRKLRFTAVPKNHQAVR.P
hu A transferase     QQLLGWPAVLRKLRFTAVPKNHQAVR.P
```

Figure 4(A)

```
  1 atgaatgtca aaggaaaagt aattctgtcg atgctggttg tctcaactgt gattgttgtg
 61 ttttgggaat atatcaacag cccagaaggc tctttcttgt ggatatatca ctcaaagaac
121 ccagaagttg atgacagcag tgctcagaag gactggtggt ttcctggctg gtttaacaat
181 gggatccaca attatcaaca agaggaagaa gacacagaca aagaaaaagg aagagaggag
241 gaacaaaaaa aggaagatga cacaacagag cttcggctat gggactggtt taatccaaag
301 aaacgcccag aggttatgac agtgacccaa tggaaggcgc cggttgtgtg ggaaggcact
361 tacaacaaag ccatcctaga aaattattat gccaaacaga aaattaccgt ggggttgacg
421 gtttttgcta ttgga
```

| | | | |
|---|---|---|---|
| Marmoset α1,3GT: | 436 | agatatattgagcattacttggaggagttcgtaacatctgctaataggtacttcatggtc | 495 |
| Human pseudogene: | 62 | .......a...t..........................a..........................t | 121 |
| Humanized α1,3GT: | 436 | ...........t..........................t..........................t | 121 |
| : | 436 | agatatattgatcattacttggaggagttcttaacatctgctaataggtacttcatggtt | 495 |

| | | | |
|---|---|---|---|
| Marmoset α1,3GT: | 496 | ggccacaaagtcatattttatgtcatggtggatgatgtctccaaggcgccgtttatagag | 555 |
| Human pseudogene: | 122 | ........................ca..........................ct.............. | 181 |
| Humanized α1,3GT: | 496 | ........................ca......................................... | 181 |
| : | 496 | ggccacaaagtcatattttacatcatggtggatgatgtctccaaggcgccgtttatagag | 555 |

| | | | |
|---|---|---|---|
| Marmoset α1,3GT: | 556 | ctgggtcctctgcgttccttcaaagtgtttgaggtcaagccagagaagaggtggcaagac | 615 |
| Human pseudogene: | 182 | ............a..........a...................................... | 241 |
| Humanized α1,3GT: | 556 | ................................................................ | 241 |
| : | 556 | ctgggtcctctgcgttccttcaaagtgtttgaggtcaagccagagaagaggtggcaagac | 615 |

| | | | |
|---|---|---|---|
| Marmoset α1,3GT: | 616 | atcagcatgatgcgtatgaagaccatcggggagcacatcttggcccacatccaacacgag | 675 |
| Human pseudogene: | 242 | ......................t..ct.................................. | 301 |
| Humanized α1,3GT: | 616 | ......................t..ct.................................. | 301 |
| : | 616 | atcagcatgatgcgtatgaagatcactggggagcacatcttggcccacatccaacacgag | 675 |

| | | | |
|---|---|---|---|
| Marmoset α1,3GT: | 676 | gttgacttcctcttctgcatggatgtggaccaggtcttccaagaccatttggggtagag | 735 |
| Human pseudogene: | 302 | ..c.........................................g... | 361 |
| Humanized α1,3GT: | 676 | ..c.........................................g... | 361 |
| : | 676 | gtcgacttcctcttctgcatggatgtggaccaggtcttccaagaccatttgggtggag | 735 |

Figure 4(B)

```
Marmoset α1,3GT:    736  accctgggccagtcggtggctcagctacaggcctggtggtacaaggcagatcctgatgac  795
Human pseudogene:   362  .....a........a...............-....c................ct.....  420

Humanized α1,3GT:   736  .....a........a....................................c......  420
                :   736  accctaggccagtcagtggctcagctacaggcctggtggtacaaggcagatcccgatgac  795

Marmoset α1,3GT:    796  tttacctatgagaggcggaaagagtcggcagcatatattccatttggccagggggatttt  855
Human pseudogene:   421  ........g......t...........a....g...c..............-.......  479

Humanized α1,3GT:   796  ...................a....g...c..............................  479
                :   796  tttacctatgagaggcggaaagagtcagcaggatacattccatttggccagggggatttt  855

Marmoset α1,3GT:    856  tattaccatgcagccattttggaggaacaccgattcaggttctcaacatcacccaggag   915
Human pseudogene:   480  ................c..........c..............................   539

Humanized α1,3GT:   856  ...............c..........................................   539
                :   856  tattaccatgcagccattttggaggaacacccattcaggttctcaacatcacccaggag   915

Marmoset α1,3GT:    916  tgctttaagggaatcctcctggacaagaaaaatgacatagaagccgagtggcatgatgaa   975
Human pseudogene:   540  .........................................a................   599

Humanized α1,3GT:   916  ...........................................................   599
                :   916  tgctttaagggaatcctcctggacaagaaaaatgacatagaagccgagtggcatgatgaa   975

Marmoset α1,3GT:    976  agccacctaaacaagtatttccttctcaacaaaccctctaaaatcttatctccagaatac  1035
Human pseudogene:   600  ................................t.................c.t.a....   659

Humanized α1,3GT:   976  ................................t.................c........   659
                :   976  agccacctaaacaagtatttccttctcaataaaccctctaaaatcttatccccagaatac  1035

Marmoset α1,3GT:   1036  tgctgggattatcatataggcctgccttcagatattaaaactgtcaagctatcatggcaa  1095
Human pseudogene:   660  ..............................................tg...g.....g   719

Humanized α1,3GT:  1036  ..................................................g.....g   719
                :  1036  tgctgggattatcatataggcctgccttcagatattaaaactgtcaagctatcgtggcag  1095

Marmoset α1,3GT:   1096  acaaaagagtataatttggttagaaagaatgtctga       1131
Human pseudogene:   720  ...........................t........       755

Humanized α1,3GT:  1096  ...........................t........       755
                :  1096  acaaaagagtataatttggttagaaataatgtctga       1131
```

GLYCOSYLTRANSFERASE VECTORS FOR TREATING CANCER

REFERENCE TO RELATED APPLICATION

This application claims priority to U.S. Patent Application No. 60/253,395; filed Nov. 27, 2000, pending. The priority application is hereby incorporated herein by reference in its entirety.

TECHNICAL FIELD

This invention relates generally to the field of virology and cancer therapy. This disclosure provides vectors in which an encoding region for glycosyltransferase is linked to a genetic element that controls transcription in a tumor or tissue specific fashion.

BACKGROUND

Many forms of cancer are intractable to traditional courses of radiation or small molecule pharmaceuticals. Considerable interest has evolved in developing gene therapy vectors as chemotherapeutic agents.

A broad variety of therapeutic genes are currently under investigation in preclinical and in clinical studies (Walther et al., Mol. Biotechnol. 13:21, 1999). The candidate genes have very different origins and different mechanisms of action—which include cytokine genes, genes coding for immunostimulatory molecules/antigens, genes encoding bacterial or viral prodrug-activating enzymes (suicide genes), and tumor suppressor genes.

Some of the putative vectors are based on adenovirus. U.S. Pat. Nos. 5,631,236 and 6,096,718 (Baylor College of Medicine) cover a method of causing regression in a solid tumor, using a vector containing an HSV thymidine kinase (tk) gene, followed by administration of a prodrug such as ganciclovir. U.S. Pat. No. 6,096,718 (Baylor College of Medicine) relates to the use of a replication incompetent adenoviral vector, comprising an HSV tk gene under control of the α-lactalbumin promoter.

U.S. Pat. Nos. 5,801,029 and 5,846,945 (Onyx Pharmaceuticals) relate to adenovirus in which the E1a gene has been altered so as not to bind and inactivate tumor suppressor p53 or RB. This prevents the virus from inactivating tumor suppression in normal cells, which means the virus cannot replicate. However, the virus will replicate in cells that have shut off p53 or RB expression through oncogenic transformation.

U.S. Pat. No. 5,998,205 (GTI/Novartis) pertains to a tissue-specific replication-conditional adenovirus, comprising a transcriptional regulatory sequence (such as the α-fetoprotein promoter) operably linked to adenovirus early replication gene. U.S. Pat. No. 5,698,443 (Calydon) provides replication-conditional adenoviruses controlled by the PSA promoter. Alemany et al. (Cancer Gene Ther. 6:21, 1999) outline complementary adenoviral vectors for oncolysis. One vector contains cis replication elements and E1a under control of a tissue-specific promoter. The supplemental vector contains all other trans-acting adenovirus replication genes. Coinfection leads to controlled killing of hepatocarcinoma cells.

International Patent Publication WO 98/14593 (Geron) describes an adenovirus construct in which the tk gene is placed under control of the promoter for telomerase reverse transcriptase (TERT). This gene is expressed at high levels in cancer cells of any tissue type, and the vector renders cancer cell lines susceptible to toxic effects of ganciclovir.

WO 00/46355 (Geron) describes an oncolytic virus having a genome in which a TERT promoter is linked to a genetic element essential for replication or assembly of the virus, wherein replication of the virus in a cancer cell leads to lysis of the cancer cell.

Koga et al. (Hu. Gene Ther. 11:1397, 2000) propose a telomerase-specific gene therapy using the hTERT gene promoter linked to the apoptosis gene Caspase-8 (FLICE). Gu et al. (Cancer Res. 60:5359, 2000) reported a binary adenoviral system that induced Bax expression via the hTERT promoter. They found that it elicited tumor-specific apoptosis in vitro and suppressed tumor growth in nude mice.

Other vectors are based on herpes family viruses, such as herpes simplex type 1 and 2. U.S. Pat. No. 5,728,379 (Georgetown University) relates to replication competent HSV containing a transcriptional regulatory sequence operatively linked to an essential HSV gene. Exemplary is the IPC4 gene under control of the pro-opiomelanocortin promoter.

Other vectors are based on the retrovirus family. U.S. Pat. No. 5,997,859 and EP 702084 B1 (Chiron) pertain to replication-defective recombinant retrovirus, carrying a vector construct capable of preventing, inhibiting, stabilizing or reversing infections, cancer, or autoimmune disease. The virus directs expression of an enzyme not normally expressed in the cells that converts a compound into a cytotoxic form. Exemplary is the HSV tk gene. WO 99/08692 proposes the use of reovirus in treating cancer, particularly ras-mediated neoplasms.

These proposed therapeutic agents are not currently approved for commercial use in the United States. There is a need to develop new constructs to improve efficacy and specificity of cancer treatment.

SUMMARY OF THE INVENTION

This invention provides a system for killing cancer cells in vitro or in vivo, using a polynucleotide encoding a glycosyltransferase under control of a tumor specific or tissue specific transcriptional control element. The glycosyltransferase typically forms a determinant on the cell surface to which some or all humans have naturally occurring antibody. In this manner, cancer cells will be culled on an ongoing basis by antibody already present in the circulation, without the need to follow the vector with an effector agent.

One embodiment of the invention is a polynucleotide as already described. Suitable glycosyltransferase enzymes include but are not limited to histo blood group A or B transferase from any upper primate (particularly human), and α(1,3)galactosyltransferase (α1,3GT) of any mammal that forms the Galα(1,3)Gal xenoantigen.

The transcriptional control element can be a tissue specific promoter, as exemplified below. Alternatively, the control element can be a tumor specific promoter, as exemplified below. Of particular interest is the promoter for telomerase reverse transcriptase (SEQ. ID NO:1). The polynucleotide can take the form of a viral vector (for example, adenovirus, herpes virus, or retrovirus), naked DNA, or a lipid composition (for example, a neutral or anionic lipid envelope, or a cationic liposome or micelle) that has a DNA or RNA component.

Polynucleotides of the invention can be used to prepare a medicament for human treatment, especially for conditions associated with hyperproliferation, such as cancer and other neoplasias.

Another embodiment of the invention is a polypeptide with glycosyltransferase activity, which comprises a consensus of mammalian α1,3GT sequences, or a humanized α1,3GT sequence, or catalytic subfragment thereof.

Also provided is a method of killing a cancer cell, comprising combining the cancer cell with a polynucleotide as already described. The invention includes a system for testing and manufacturing the glycosyltransferase vectors of this invention. The invention can be used for treating cancer in a subject by administering to the subject a polynucleotide as already described.

Other embodiments of the invention will be apparent from the description that follows.

DRAWINGS

Figure 1:
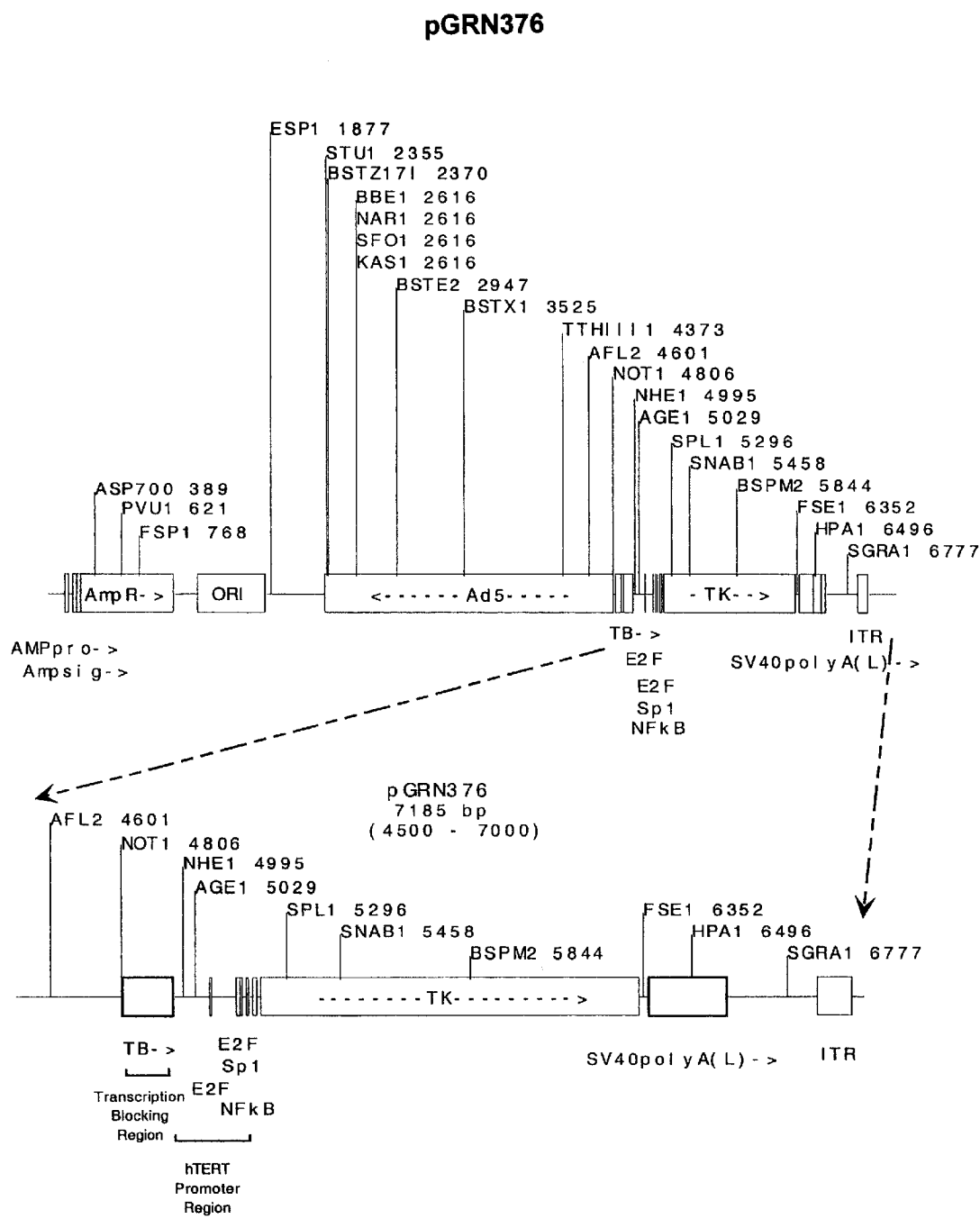
FIG. 1 is a map of adenovirus vector designated pGRN376, in which the promoter for telomerase reverse transcriptase (TERT) controls expression of the tk gene (Example 1).

FIG. 3 is a sequence listing comparing the human blood group A and B transferase amino acid sequences with α(1,3) galactosyltransferase (α1,3GT) of other species. A consensus version and a humanized version of α1,3GT are shown as SEQ. ID NOs:12 & 13. (−) represents a sequence gap; (.) indicates a residue identical with the aligned marmoset α1,3GT sequence (Example 3). Other sequences shown in this figure are listed in Table 2.

FIG. 4 is a sequence listing comparing the marmoset α1,3GT encoding sequence with the human α1,3GT pseudogene. The humanized α1,3GT encoding sequence is shown as SEQ. ID NO:16 (Example 3). The sequences shown in this figure are listed in Table 2.

DETAILED DESCRIPTION

A long-sought objective in cancer treatment is to design a therapeutic agent that effectively kills cancer cells wherever they are located, while sparing other cells in the vicinity that do not bear the malignant phenotype.

The invention described in this disclosure solves the problem by providing a therapeutic vector that encodes an enzyme that forms a target molecule on the cell surface that can be targeted by antibody in situ. Particularly effective are so-called natural antibodies that recognize features of foreign complex carbohydrates. A number of naturally occurring anti-carbohydrate antibodies are present in the circulation of humans without deliberate immunization. It is thought that these antibodies arise from cross-reacting mucins and other carbohydrate-bearing substances that people are routinely exposed to through their diet.

In one aspect of this invention, the carbohydrate targets are produced in greater abundance on tumor cells, because expression of the enzyme that makes the target is controlled by a transcriptional control element that is tumor or tissue specific. Tumor-specific targeting relies on control elements taken from genes expressed predominantly in cells that undergo repeated proliferation, or that are relatively undifferentiated. Such vectors are effective for treating a wide variety of tumor types at the primary site or elsewhere. Tissue-specific targeting relies on control elements taken from genes expressed in particular tissue types. Such vectors are especially useful for treating metastases, or tumors in which the tissue-specific element is relatively more abundant.

Treatment is effected by administering the vector systemically or locally so that it can migrate to and transfect the tumor cells causing the disease. The vector then causes expression of the new carbohydrate structure at the cell surface. This becomes a target for antibody in the circulation (or other components of the immune system, such as cytotoxic T cells, ADCC cells, or T helper/inducer cells)—which in turn leads to a number of possible effects—complement-mediated lysis, opsonization, cytotoxic killing, cytokine and interferon secretion, and inflammatory response.

This system is believed to offer two advantages over previous approaches to gene therapy for cancer.

The first advantage is that it can provide ongoing surveillance against the emergence of new malignancies. This is available when using a tumor-specific expression vector, such as the TERT promoter described below, and when the vector is capable of replication or remains expressible by the cell. In cancer cells, the vector will cause expression of the target carbohydrate, causing them to be recognized and eliminated by antibody. In cells that are not actively malignant, the vector will remain quiescent—until such time as the cell reverts to the cancer phenotype—whereupon the target carbohydrate will be expressed de novo, and the cell becomes eliminated in its turn. Since naturally occurring antibody is persistently available, there is no need to readminister an effector drug to eradicate any newly activated cancer cells.

The second advantage is that glycosyltransferases potentially provide a second level of specificity for malignant cells. In using tumor-specific promoters to drive gene expression, there is at least a theoretical concern that the vector may also have an effect on non-cancerous cells that up-regulate the promoter transiently as part of the normal replicative process of the cell. For example, TERT is expressed transiently by some actively growing stem cells, lymphocytes, and germinal tissue.

The potential second layer of specificity provided by glycosyltransferase is related to the density of carbohydrate determinants on the surface of certain types of progenitor cells. Immune lysis of cells through glycolipid antigen depends primarily on IgG antibody. The IgG molecule must span two antigenic determinants with its two combining sites in order to activate complement—binding to only one determinant (termed monogamous bivalency) is insufficient. This means there is a minimum density of determinants that must be present in order for the antibody to activate complement.

Fetal red cells bear a low density of ABO blood group determinants, attributable to paucity of branches in the oligosaccharide. This means that ABO blood group IgG antibodies can only bind monogamously (Romans et al., J. Immunol. 124:2807, 1980). If other fetal and embryonic cells express the branching enzyme in the same limited fashion, then they may also be less susceptible to complement lysis mediated by antibodies directed against any part of the same complex carbohydrate.

This theoretical rationale is provided to enhance the reader's appreciation of the invention. Those skilled in the art will appreciate that there are other advantages in the invention beyond those indicated above. This explanation is not meant to limit the claimed invention in any way.

Further explanation of the making and use of the vector constructs of the invention is provided in the sections that follow.

Definitions

The term "polynucleotide" refers to a polymeric form of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refer interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A "control element" or "control sequence" is a nucleotide sequence that contributes to the functional regulation of a polynucleotide, such as replication, duplication, transcription, splicing, translation, or degradation of the polynucleotide. Transcriptional control elements include promoters, enhancers, and repressors.

Particular gene sequences referred to as promoters, like the "TERT promoter", or the "PSA promoter", are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans may comprise a segment that at least 90% identical to a promoter sequence of a human gene. A particular sequence can be tested for activity and specificity, for example, by operatively linking to a reporter gene (Example 1).

Genetic elements are said to be "operatively linked" if they are in a structural relationship permitting them to operate in a manner according to their expected function. For instance, if a promoter helps initiate transcription of the coding sequence, the coding sequence can be referred to as operatively linked to (or under control of) the promoter. There may be intervening sequence between the promoter and coding region so long as this functional relationship is maintained.

In the context of encoding sequences, promoters, and other gene elements, the term "heterologous" indicates that the element is derived from a genotypically distinct entity from that of the rest of the entity to which it is being compared. For example, a promoter or gene introduced by genetic engineering techniques into a context; in which it does not occur in nature is said to be a heterologous polynucleotide. An "endogenous" genetic element is an element that is in the same place in the chromosome where it occurs in nature, although other gene elements may be artificially introduced into a neighboring position.

The terms "polypeptide", "peptide" and "protein" are used interchangeably to refer to polymers of amino acids of any length. The polymer may comprise modified amino acids, it may be linear or branched, and it may be interrupted by non-amino acids.

The term "antibody" as used in this disclosure refers to both polyclonal and monoclonal antibody. The ambit of the term deliberately encompasses not only intact immunoglobulin molecules, but also such fragments and genetically engineered derivatives of immunoglobulin molecules, T cell receptors, and their equivalents as may be prepared by techniques known in the art, and which retain binding specificity of the antigen combining site.

General Techniques

Methods in molecular genetics and genetic engineering are described generally in the current editions of *Molecular Cloning: A Laboratory Manual*, (Sambrook et al.); *Oligonucleotide Synthesis* (M. J. Gait, ed.,); *Animal Cell Culture* (R. I. Freshney, ed.); *Gene Transfer Vectors for Mammalian Cells* (Miller & Calos, eds.); *Current Protocols in Molecular Biology and Short Protocols in Molecular Biology, 3rd Edition* (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

For a description of the molecular biology of cancer, the reader is referred to *Principles of Molecular Oncology* (M. H. Bronchud et al. eds., Humana Press, 2000); *The Biological Basis of Cancer* (R. G. McKinnel et al. eds., Cambridge University Press, 1998); and *Molecular Genetics of Cancer* (J. K. Cowell ed., Bios Scientific Publishers, 1999).

General techniques for the development, testing, and administration of biomolecular chemotherapeutics are provided in *Gene Therapy of Cancer*, Adv. Exp. Med. Biol. vol. 451 (P. Walden ed., Plenum Publishing Corp., 1998); *Cancer Gene Therapy*, Adv. Exp. Med. Biol. vol. 465(N. A. Habib ed., Kluwer Academic Pub, 2000); and *Gene Therapy of Cancer: Methods and Protocols*, Meth. Mol. Med. vol. 35 (W. Walther & U. Stein eds., Humana Press, 2000).

Effector Genes for Tumor Cell Depletion

The vectors of this invention comprise an encoding region that forms a carbohydrate determinant on the cell surface as a target for cancer cell lysis.

Exemplary are glycosyltransferases that synthesize an alloantigen or xenoantigen widely expressed on different tissue types.

In humans, an $\alpha(1,2)$fucosyltransferase uses N-acetyl lactosamine acceptor groups on cell surface glycoproteins and glycolipids to form Fuc$\alpha(1,2)$Gal$\beta(1,4)$GlcNAc, which is blood group H substance. This in turn serves as an acceptor for the ABO histo blood group transferases, which form terminal allodeterminants on the complex carbohydrate. Blood group A transferase adds GalNAc to form GalNAc$\alpha(1,3)$Gal (A substance). Blood group B transferase adds Gal instead to form Gal$\alpha(1,3)$Gal (B substance).

According to the blood group of an individual, one or both of these transferases are expressed in essentially all nucleated cells, resulting in expression of A and B substance on the cell surface. Red cells also abundantly present A and B substance, by virtue of synthesis before enucleation, and subsequent adsorption of glycolipids from plasma. Naturally occurring antibodies circulate in the blood that react against the ABO determinants that are not self-antigens. One advantage of using an ABO transferase as the effector sequence is that the H precursor substance will be available on the surface membrane of virtually any tumor.

The nucleotide and protein sequence of A transferase and B transferase are provided below. See also U.S. Pat. Nos. 5,068,191 and 5,326,857. The two enzymes are close homologs of each other, differing by only a few amino acids. Another advantage of using an ABO transferase as the effector sequence is that the expressed protein is of human origin, and unlikely to be immunogenic by virtue of its similarity to another gene product expressed as a self antigen in the patient being treated.

Mammals other than humans, apes and Old World monkeys do not form H precursor substance, but instead convert the N-acetyl lactosamine acceptor into the Galα(1,3)Gal determinant. Galα(1,3)Gal epitope is expressed prominently on the surface of nucleated cells, including hepatic cells, renal cells, and vascular endothelium—and is the main target for the natural antibodies mediating xenograft rejection (reviewed by Joziasse et al., Biochim. Biophys. Acta 1455:403, 1999; Sandrin et al., Frontiers Biosci. 2:31, 1997).

The Galα(1,3)Gal epitope is made by a specific enzyme, α(1,3)galactosyltransferase (α1,3GT). In humans and other primates that don't express the Galα(1,3)Gal product, the α1,3GT locus is inactivated (Gailili et al., Proc. Natl. Acad. Sci. USA 15:7401, 1991). There are frameshift and nonsense mutations within the locus, turning it into a non-functional, processed pseudogene (Laarsen et al., J. Biol. Chem. 265:7055, 1990; Joziasse et al., J. Biol. Chem. 266:6991, 1991).

For use in this invention, α1,3GT of any species can be used. A number of α1,3GT sequences are provided below. For use in human therapy, it may be beneficial to use an α1,3GT that differs as little as possible from the human pseudogene sequence, while retaining the same specificity. The complete marmoset α1,3GT sequence is provided below, and can be humanized by substituting residues from the human pseudogene that do not alter the binding or catalytic site. If desired, glycosyltransferases can also be truncated down to the minimal size of the catalytically active enzyme (Henion et al., Glycobiology 4:193, 1994).

Other glycosyltransferases can also be identified for use in this invention. Candidates include transferases responsible for other carbohydrate blood group alloantigens (for example, Lewis, P, li blood groups). Candidates also include non-mammalian glycosyltransferases, and transferases responsible for making determinants present on embryonic cells of humans and other species that are not found on most adult cells.

The choice of a particular transferase may involve a number of considerations and routine empirical testing. One consideration is the density of determinants formed on transfected cells. As discussed earlier, certain glycosyltransferases may synthesize a lower density of determinants on stem cells by virtue of the relative paucity of branched precursor substances on those cells. By judicious selection of the transferase, it may be possible to titrated the density of determinants formed. For example, A- and B-transferases will have exclusive access to H substance if transfected into type O cells, or will compete 1:1 with each other as counterparts. α1,3GT is expected to produce less determinant, because it must compete in humans with the α(1,2)fucosyltransferase that forms H substance. It has been found that α1,3GT fairs less well in this competition because of its position in the Golgi, which in turn is a function of the N-terminal membrane-anchoring domain. It is possible to switch the α(1,2)fucosyltransferase cytoplasmic domain onto α1,3GT in order to increase the density of Galα(1,3) Gal epitopes produced (Osman et al., J. Biol. Chem. 271:33105, 1996).

Transcriptional Control Elements for Tumor Targeting

The control element is selected with a view to the protein expression patterns in cancer cells compared with non-malignant cells that will also be exposed to the vector.

Many tumor-specific transcriptional control elements can be used in this invention. These control elements cause elevated transcription of the encoding sequence they are linked to in tumor cells of a variety of different types. Examples are promoters that control telomerase reverse transcriptase (TERT), carcinoembryonic antigen (CEA), hypoxia-responsive element (HRE), autocrine motility factor receptor (Grp78), L-plastin, and hexokinase II.

The promoter for TERT is exemplary. Sequence of the human TERT gene (including upstream promoter sequence) is provided below. The reader is also referred to U.K. Patent GB 2321642 B (Cech et al., Geron Corporation and U. Colorado), International Patent Publications WO 00/46355 (Morin et al., Geron Corporation), WO 99/33998 (Hagen et al., Bayer Aktiengesellschaft), and Horikawa et al. (Cancer Res., 59:826, 1999). Other TERT sequences can also be used; the mouse sequence is provided in WO 99/27113 (Morin et al., Geron Corporation). A lambda phage clone designated λGΦ5, containing ~13,500 bases upstream from the hTERT encoding sequence, is available from the ATCC under Accession No. 98505. Example 1 illustrates the testing and use of TERT promoter sequences in vector expression systems. Those skilled in the art will appreciate that promoter sequences not contained in λGΦ5 but homologous and capable of promoting preferential expression in cancer cells can be used with similar effect. For example, a TERT promoter can comprise a sequence of 25, 50, 100, or 200 consecutive nucleotides that is 80%, 90%, or 100% identical (or can hybridize under stringent conditions) to a sequence contained in SEQ. ID NO:1.

As an alternative, a transcriptional control element can be used that is tissue-specific. Constructs of this kind will cause preferential expression of the glycosyltransferase, if the level of expression of the endogenous gene is higher in tumor cells than in non-malignant tissue of the same type. They are also useful to treat tumors that have metastasized away from the primary site. Examples are promoters that control transcription of albumin (liver-specific), a-fetoprotein (AFP, liver-specific), prostate-specific antigen (PSA, prostate-specific), mitochondrial creatine kinase (MCK, muscle-specific), myelin basic protein (MBP, oligodendrocyte-specific), glial fibrillary acidic protein (GFAP, glial cell specific), and neuron-specific enolase (NSE, neuron-specific). See U.S. Pat. No. 5,871,726 (Calydon), WO 98/39466 (Calydon), U.S. Pat. No. 5,998, 205 (Genetic Therapy Inc.).

Additional promoters suitable for use in this invention can be taken from other genes that are preferentially expressed in tumor cells. Such genes can be identified, for example, by differential display and comparative genomic hybridization: see U.S. Pat. Nos. 5,759,776 and 5,776,683. Alternatively, microarray analysis can be performed cDNA fragments of candidate genes in a 96 or 384 well format, and then spotted directly onto glass slides. To compare mRNA preparations from cancer cells and a matched non-malignant control, one preparation is converted into Cy3-labeled cDNA, while the other is converted into Cy5-labeled cDNA. The two cDNA preparations are hybridized simultaneously to the microarray slide, and then washed to eliminate non-specific binding. Any given spot on the array will bind each of the cDNA products in proportion to abundance of the transcript in the two original mRNA preparations. The slide is then scanned at wavelengths appropriate for each of the labels, and the relative abundance of mRNA is determined. Preferably, the level of expression of the effector gene will be at least 5-fold or even 25-fold higher in the undifferentiated cells relative to the differentiated cells. Having identified transcriptional control elements of interest, specificity can be tested in a reporter construct where the control element is used to control transcription of a reporter gene, such as green fluorescence protein, secreted alkaline phosphatase, or β-galactosidase.

Formulation and Administration of Cancer Therapeutics

A number of viral vectors are suitable for cancer gene therapy according to the invention. For general principles in vector construction, the reader is referred to *Viral Vectors for Gene Therapy* (B. J. Carter, Biotechnology 1999, XVIII, 562 p. 393, 1999).

Adenovirus vectors provide transient gene expression, and can be constructed to be replication competent or replication incompetent. For general principles in adenovirus construction, see Danthinne et al., Gene Ther. 7:1707, 2000, Bilbao et al., Adv. Exp. med. Biol. 451:365, 1998, and U.S. Pat. No. 5,631,236 (Baylor College of Medicine), U.S. Pat. No. 5,670,488 (Genzyme), U.S. Pat. No. 5,698,443 (Calydon), U.S. Pat. No. 5,712,136 (GenVec), U.S. Pat. No. 5,880,102 (Duke University), U.S. Pat. No. 5,994,128 (IntroGene), U.S. Pat. No. 6,040,174 (Transgene), U.S. Pat. No. 6,096,718 (Gene Targeting Corp).

Retrovirus vectors can be constructed to provide gene expression that is inheritable by progeny of the cell it infects. U.S. Pat. Nos. 5,698,446 and 6,133,029 (Chiron). Vectors can also be based on viruses of the herpes family. U.S. Pat. No. 5,728,379 (Georgetown University). Adeno-associated virus, reovirus, and a number of other viruses are also suitable.

As an alternative, the vectors of this invention can be constructed on a technology which is not virus based. Suitable are nucleic acid-lipid complexes of various kinds, where the lipid protects the nucleic acid en route to the tumor, and facilitates entry into the cell. One form is cationic liposomes or micelles. Li et al. (Gene Ther. 5:930, 1998) generally describe cationic lipid—promoter—DNA complexes for intravenous gene delivery. Another form is neutral or anionic liposomes, where the DNA is encapsulated in a lipid envelope that may express other components to inhibit non-specific uptake. U.S. Pat. No. 5,981,501 (Inex) and U.S. Pat. No. 6,043,094 (Sequus/Alza). The composition may resemble an artificial viral envelope. U.S. Pat. No. 5,766,625 (U. Florida) and WO 97/04748 (Advanced Therapies).

Also part of the invention are viral constructs in which gene expression is cell-specific, and the virus itself is replication conditional. See generally Todo et al., Cancer Gene Ther. 7:939, 2000; and WO 00/46355 (Geron). In this embodiment, the glycosyltransferase encoding region is under control of a tissue or tumor specific control element—and a gene essential for replication or packaging of the virus is also under control of a tissue or tumor-specific control element. Genes required for replication of adenovirus include E1a, E1b, E2, and E4. Genes required for replication of HSV include ICP6 and ICP4. Glycosyltransferase expression and viral replication can be controlled by the same promoter—or they can be controlled by different promoters, providing a further level of specificity for cancer cells.

Constructs comprising different glycosyltransferase encoding regions and different regulatory control elements can be tested and compared in several different assay systems. Suitable cells for these assays include human tumor cells expressing the gene from which the regulatory control element of the virus is taken (e.g., hTERT), matched with cell lines from a similar non-malignant tissue, or a tissue expressing about the same density of acceptor substrate for the glycosyltransferase. The cells can be transduced with the test vector, with a vector not comprising the glycosyltransferase sequence (negative control), and with a vector in which the glycosyltransferase is under control of a constitutive promoter (such as CMV or PGK).

Expression of the glycosyltransferase can be detected at the RNA level by RT-PCR, and at the protein level by immunocytochemistry, according to standard techniques. Expression of the cell-surface determinant synthesized by the glycosyltransferase can be detected using epitope-specific antibody or lectin, for example, by FACS. Human type B serum contains antibodies to A substance and to the Galα(1,3)Gal xenoantigen. The "IB4" lectin from Bandeiraea (Griffonia) simplicifolia (Sigma Cat. L 3019) is specific for α-D-galactosyl residues and binds both the Galα(1,3)Gal epitope, and B blood group substance. Antigen density can be compared for vectors with different promoters and effectors in quantitative assays using labeled monovalent antibody. Monogamous bivalency (the ability or inability of specific IgG to bind by more than one combining site) can be measured in suspended cells using the antiglobulin test (Romans et al., J. Immunol. 124:2807, 1980).

Ultimately, efficacy of the constructs of this invention can be assessed by their ability to trigger complement-mediated tumor cell lysis. A panel of tumor and non-tumor lines in culture is transfected with the vector, and then exposed to a source of epitope-specific antibody plus complement. For typical vectors encoding α1,3GT, fresh human serum will contain sufficient antibody and complement to cause specific lysis. For typical vectors encoding an A or B transferase, fresh serum of O blood type should cause lysis. If fresh serum is not available for the product of a particular glycosyltransferase, lysis can be measured using specific antibody and guinea pig complement. Rather than measuring lysis, the cells can be treated for a brief interval and then injected into a suitable mouse model, to determine if the treatment inhibits tumor growth.

General validation of the approach and titration of virus can be confirmed using a α1,3GT vector in α1,3GT knock-out mice. U.S. Pat. No. 5,849,991 (Bresatch) reports mice that are homozygous for inactivated α1,3GT, resulting in lack of expression of Galα(1,3)Gal epitope, as determined by specific antibody. A model is developed in which the mice are injected with a representative human cancer cell line, such as a glioma. After solid tumors have developed of a sizeable diameter, the mice are injected intravenously or intratumorally with the α1,3GT vector. A dose of $10^5$ to $10^8$ pfu is the predicted test range for HSV vectors. Once the α1,3GT is expressed, anti-Galα(1,3)Gal in the plasma of these mice should opsonize the tumor cells, slowing tumor growth, potentially causing regression and increased survival.

Treatment of human patients having a tumor depends on the nature of the vectors available and the carbohydrate determinants naturally expressed on their cells. Patients of blood type O (~46% of the U.S. population) will have natural antibody to both A and B substance, and can be treated with a vector encoding either A or B transferase. Patients of blood type A (~38%) or B (~12%) will have natural antibody to the opposite determinant, and can be treated with a vector encoding the corresponding transferases. Patients of blood type AB (~4% of the population) will not be treatable using either vector. It is possible to use a mixture of A and B transferase vectors as a universal reagent for patients of blood types A, B, and O (~96% of the population). The lytic potential of the mixture may be somewhat reduced in blood types A and B, since the transferases will be codominantly expressed.

A universal reagent suitable for treating all ABO blood groups is a vector made using the α1,3GT transferase. Since humans don't have the anti-Galα(1,3)Gal epitope, essentially everyone should have naturally occurring antibody. α1,3GT must compete in humans for the N-acetyl lactosamine acceptor substrate with the α(1,2) fucosyltransferase that makes H substance. Since α1,3GT fairs less well in this competition because of its position in the Golgi (Osman et al., J. Biol. Chem. 271:33105, 1996), a higher density of epitope will be formed by a construct that encodes the N-terminal membrane anchoring domain of the α(1,2)fucosyltransferase fused to the extramembrane catalytic domain of α1,3GT.

Dosage and formulation of medicaments intended for human therapy are designed based on the animal model experiments. For general guidance on formulation and testing of medicament formulations for human administration, the reader is referred to *Biopharmaceutical Drug Design and Development* (S. Wu-Pong et al. eds, Humana Press 1999); *Biopharmaceuticals: Biochemistry and Biotechnology* (G. Walsh, John Wiley & Sons, 1998); and the most current edition of *Remington: The Science and Practice of Pharmacy* (A. Gennaro, Lippincott, Williams & Wilkins). Pharmaceutical compositions of this invention may be packaged in a container with written instructions for use of the cells in human therapy, and the treatment of cancer.

The Examples that Follow are Provided by Way of Further Illustration, and are not Meant to Limit the Claimed Invention.

EXAMPLES

Example 1
Preparation of Vectors Controlling Transcription in Cells Expressing Telomerase Reverse Transcriptase The lambda clone designated λGΦ5 containing the hTERT promoter is deposited with the American Type Culture Collection (ATCC), 10801 University Blvd., Manassas, Va. 20110 U.S.A., under Accession No. 98505. λGΦ5 contains a 15.3 kbp insert including approximately 13,500 bases upstream from the hTERT coding sequence.

A Not1 fragment containing the hTERT promoter sequences was subcloned into the Not1 site of pUC derived plasmid, which was designated pGRN142. A subclone (plasmid pGRN140) containing a 9 kb Ncol fragment (with hTERT gene sequence and about 4 to 5 kb of lambda vector sequence) was partially sequenced to determine the orientation of the insert. pGRN140 was digested using SalI to remove lambda vector sequences, the resulting plasmid (with removed lambda sequences) designated pGRN144. The pGRN144 insert was then sequenced.

SEQ. ID NO:1 is a listing of the sequence data obtained. Nucleotides 1–43 and 15376–15418 are plasmid sequence. Thus, the genomic insert begins at residue 44 and ends at residue 15375. The beginning of the cloned cDNA fragment corresponds to residue 13490. There are Alu sequence elements located ~1700 base pairs upstream. The sequence of the hTERT insert of pGRN142 can now be obtained from GenBank under Accession PGRN142.INS AF121948. Numbering of hTERT residues for plasmids in the following description begins from the translation initiation codon, according to standard practice in the field. The hTERT ATG codon (the translation initiation site) begins at residue 13545 of SEQ. ID NO:1. Thus, position –1, the first upstream residue, corresponds to nucleotide 13544 in SEQ. ID NO:1.

Expression studies were conducted with reporter constructs comprising various hTERT upstream and intron sequences. A BglII-Eco47III fragment from pGRN144 (described above) was digested and cloned into the BglII-NruI site of pSEAP2Basic (ClonTech, San Diego, Calif.) to produce plasmid designated pGRN148. A second reporter-promoter, plasmid pGRN150 was made by inserting the BglIII-FspI fragment from pGRN144 into the BglIII-NruI sites of pSEAP2. Plasmid pGRN173 was constructed by using the EcoRV-StuI (from +445 to –2482) fragment from pGRN144. This makes a promoter reporter plasmid that contains the promoter region of hTERT from approximately 2.5 kb upstream from the start of the hTERT open reading frame to just after the first intron within the coding region, with the initiating Met codon of the hTERT open reading frame changed to Leu. Plasmid pGRN175 was made by APA1 (Kienow blunt)-SRF1 digestion and religation of pGRN150 to delete most of the Genomic sequence upstream of hTERT. This makes a promoter/reporter plasmid that uses 82 nucleotides of hTERT upstream sequences (from position –36 to –117). Plasmid pGRN176 was made by PML1-SRF1 religation of pGRN150 to delete most of the hTERT upstream sequences. This makes a promoter/reporter plasmid that uses 204 nucleotides of hTERT upstream sequences (from position –36 to –239).

Levels of secreted placental alkaline phosphatase (SEAP) activity were detected using the chemiluminescent substrate CSPDTM (ClonTech). SEAP activity detected in the culture medium was found to be directly proportional to changes in intracellular concentrations of SEAP mRNA. The pGRN148 and pGRN150 plasmids (hTERT promoter-reporter) and the pSEAP2 plasmid (positive control, containing the SV40 early promoter and enhancer) were transfected into test cell lines. pGRN148 and pGRN150 constructs drove SEAP expression as efficiently as the pSEAP2 in immortal (tumor-derived) cell lines. Only the pSEAP2 control gave detectable activity in mortal cells.

The ability of the hTERT promoter to specifically drive the expression of the thymidine kinase (tk) gene in tumor cells was tested using a variety of constructs: One construct, designated pGRN266, contains an EcoRI-FseI PCR fragment with the tk gene cloned into the EcoRI-FseI sites of pGRN263. pGRN263, containing approximately 2.5 kb of hTERT promoter sequence, is similar to pGRN150, but contains a neomycin gene as selection marker. pGRN267 contains an EcoRI-FseI PCR fragment with the tk gene cloned into the EcoRI-FseI sites of pGRN264. pGRN264, containing approximately 210 bp of hTERT promoter sequence, is similar to pGRN176, but contains a neomycin gene as selection marker. pGRN268 contains an EcoRI-XbaI PCR fragment with the tk gene cloned into the EcoRI-XbaI (unmethylated) sites of pGRN265. pGRN265, containing approximately 90 bp of hTERT promoter sequence, is similar to pGRN175, but contains a neomycin gene as selection marker.

These hTERT promoter/tk constructs, pGRN266, pGRN267 and pGRN268, were re-introduced into mammalian cells and tk/+ stable clones (and/or mass populations) were selected. Ganciclovir treatment in vitro of the tk/+ cells resulted in selective destruction of all tumor lines tested, including 143B, 293, HT1080, Bxpc-3', DAOY and NIH3T3. Ganciclovir treatment had no effect on normal BJ cells.

FIG. 1 is a map of the TPAC adenovector pGRN376. It was made by cloning the NOT1-BAMH1 fragment from pGRN267 into the NOT1-BGL2 sites of pAdBN (Quantum Biotech). The 7185 bp vector comprises the herpes simplex thymidine kinase (tk) gene under control of the medium-length hTERT promoter sequence.

Example 2
Killing Cancer Cells Using Vectors Controlled by the TERT Promoter A replication-conditional adenovirus was constructed by placing a gene involved in viral replication under control of the hTERT promoter, which should activate transcription in telomerase-expressing cancer cells. The viral construct comprised the Inverted Terminal Repeat (ITR) from adenovirus Ad2; followed by the hTERT medium-length promoter (phTERT176) operably linked to the adenovirus E1a region; followed by the rest of the adenovirus deleted for the E3 region (ΔE3). As a positive control, a similar construct was made in which E1a was placed under control of the CMV promoter, which should activate transcription in any cell.

infected at an MOI=20, ~24h post plating. The cells were then cultured over a period of 17–48 days, and fed every fourth day. The pictures shown in the Figure were taken 7 days after infection. The top row of each section shows the results of cells that were not virally infected (negative control). The middle row shows the results of cells infected with oncolytic adenovirus, in which replication gene E1a is operably linked to the hTERT promoter. The bottom row of each section shows the results of cells infected with adenovirus in which E1a is operably linked to the CMV promoter (positive control). Results are summarized in Table 1.

TABLE 1

Effect of Oncolytic Virus on Cancerous and Non-cancerous Cells

| Cell Line | Origin | Culture Conditions | Uninfected cell Lysis | Lysis by phTERT-E1ΔE3 | Lysis by pCMV-E1ΔE3 |
|---|---|---|---|---|---|
| BJ | foreskin fibroblast | 90% DMEM/M199 + 10% FBS | NO | NO | YES |
| IMR | lung fibroblast | 90% DMEM/M199 + 10% FBS | NO | NO | YES |
| WI-38 | lung fibroblast | 90% DMEM/M199 + 10% FBS + 5 μg mL gentamicin | NO | NO | YES |
| A549 | lung carcinoma | 90% RPMI + 10% FBS | NO | YES | YES |
| AsPC-1 | adenocarcinoma, pancreas | 90% RPMI + 10% FBS | NO | YES | YES |
| BxPC-3 | adenocarcinoma, pancreas | 90% EMEM + 10% FBS | NO | YES | YES |
| DAOY | medulloblastoma | 90% EMEM + 10% FBS | NO | YES | YES |
| HeLa: | cervical carcinoma | 90% EMEM + 10% FBS | NO | YES | YES |
| HT1080 | fibrosarcoma | 90% EMEM + 10% FBS | NO | YES | YES |

Reagents were obtained as follows. pBR322, restriction enzymes: NEB, Beverly, Mass. Adenovirus Type 2 (Ad2), tissue culture reagents: Gibco/BRL, Grand Island, N.Y. Profection Mammalian Transfection Systems: Promega, Madison, Wis. Tumor and Normal Cell lines: ATCC, Manassas, Va., except BJ line, which was obtained from J. Smith, U. of Texas Southwestern Medical Center.

Briefly, a pBR322-based plasmid was constructed which contains the Adenovirus Type 2 genome with deletions from 356–548nt (E1a promoter region) and 27971–30937nt (E3). A multiple cloning region was inserted at the point of deletion of the E1a promoter, and hTERT promoter (−239 to −36nt) or CMV promoter (−524 to −9nt) was subsequently cloned. Numbering of the CMV sequence is in accordance with Akrigg et al., Virus Res. 2:107, 1985. Numbering of the Ad2 sequence is in accordance with "DNA Tumor Viruses: Molecular Biology of Tumor Viruses", J. Tooze ed., Cold Spring Harbor Laboratory, NY. These plasmid DNAs were digested with SnaBI to liberate ITRs, then phenol-chloroform extracted, precipitated and transfected into 293A cells for propagation of the virus. Several rounds of plaque purifications were performed using A549 cells, and a final isolate was expanded on these same cells. Viruses were titered by plaque assay on 293A cells, and tested for the presence of 5' WT Ad sequences by PCR. DNA was isolated from viruses by HIRT extraction.

Figure 2:
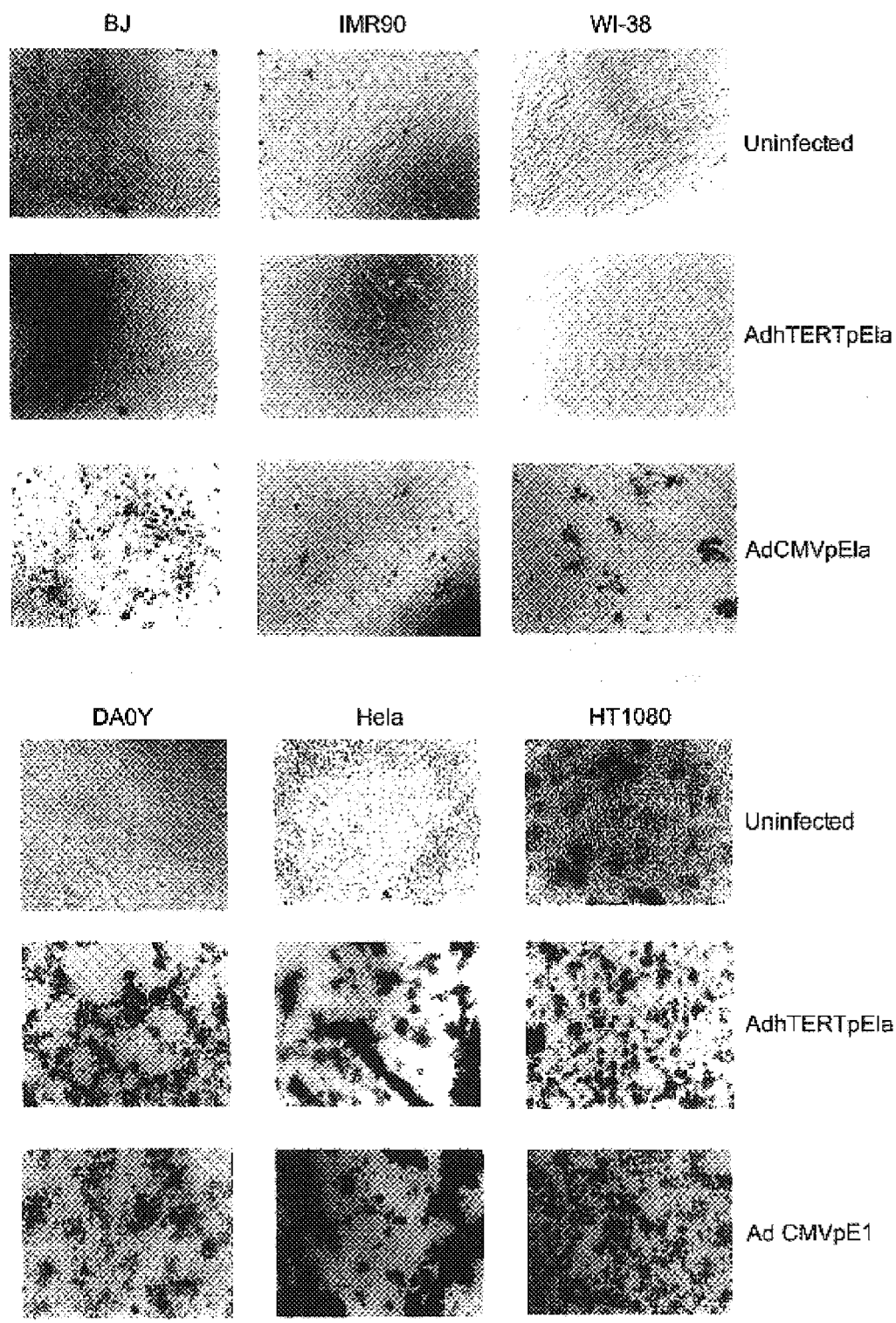
FIG. 2 is a photographic reproduction showing the effects of replication-conditional adenovirus on normal and cancer-derived cell lines (Example 2).

FIG. 2 shows the effect of these viruses on normal and cancer-derived cell lines. Each cell line was plated and All cell lines tested were efficiently lysed by AdCMV-E1 dIE3 by day 17 post-infection. All tumor lines were lysed by AdphTERT-E1dIE3 in a similar, but slightly delayed period, while normal lines showed no signs of cytopathic effect and remained healthy out to 6 weeks post-infection.

The results demonstrate that an oncolytic virus can be constructed by placing a genetic element essential for replication of the virus under control of an hTERT promoter. Replication and lysis occurs in cancer cells, but not in differentiated non-malignant cells.

Example 3
Killing Cancer Cells Using Glycosyltransferase Vectors and Natural Antibody Adenovirus vectors comprising encoding sequences for glycosyltransferase under control of the TERT promoter are constructed by cloning the encoding sequence behind the hTERT promoter sequence of pGRN267, as described in Example 1.

SEQ. ID NO:2 and SEQ. ID NO:4 provide the encoding sequences for the A and B transferase, respectively.

FIG. 3 is a comparison of the known mammalian α1,3GT protein sequences, the ABO transferases, and the amino acid translation of the human α1,3GT pseudogene. Based on this comparison and a comparison of the gene sequences, a humanized version of the marmoset α1,3GT protein sequence has been devised (SEQ. ID NO:13). Another α1,3GT sequence has been devised in which the marmoset prototype has been adapted with substitutions in the extracellular domain to enhance activity, based on a consensus of other mammalian α1,3GT amino acid sequences (SEQ. ID NO:12).

FIG. 4 provides a listing of a humanized α1,3GT encoding sequence, adapting the marmoset nucleic acid sequence with conservative and silent substitutions in the human pseudogene (SEQ. ID NO:16).

A model adenovirus vector is made using the sheep α1,3GT encoding sequence shown in SEQ. ID NO:17. Briefly, a EcI136II fragment from a plasmid comprising the cDNA coding sequence plus ~70 bp of untranslated upstream sequence is cloned into the EcoRI(Klenow blunted)-FseI(Klenow blunted) sites of pGRN267 such that the sheep α1,3GT gene is in the same orientation as the hTERT promoter. Then a NotI-BamHI fragment from the plasmid containing the transcription pause region, the hTERT promoter, the sheep α1,3GT gene sequence and the SV40 polyA signal is cloned into the NotI-BglII sites of pAdBN (Quantum), which is then made into an adenovirus vector according to the manufacturer's technology.

Ability of α1,3GT and ABO transferase vectors to promote tumor cell lysis is tested using a panel of established cell lines as in Example 2.

First, the ABO phenotype of each line is determined by incubating alternate wells with fresh human serum of the A and B blood type at 37° C. for 30–60 min, and measuring trypan blue exclusion.

Fresh cells are then transduced with the test vectors at a suitable MOI, and cultured in a serum-free medium. Vectors comprising the opposite ABO transferase or α1,3GT under control of the TERT promoter are used to treat the test well. The same transferase under control of the CMV promoter is a positive control. A promoterless vector, a vector comprising ABO matched transferase, and empty vector can all serve as negative controls.

After 2 or 7 days, the cells are washed, and overlaid with fresh ABO matched human serum. After incubation at 37° C. for 30–60 min, 0.4% trypan blue is added, and the percentage of lysed (blue staining) cells is determined.

TABLE 2

Sequences listed in this Disclosure

| SEQ. ID NO: | Designation | Reference |
|---|---|---|
| 1 | Lambda clone designated λGφ5 (ATCC Accession No. 98505) Contains human Telomerase Reverse Transcriptase (hTERT) genomic insert (residues 44–15375). The ATG translation initiation site begins at residue 13545. | GenBank Accession AF121948 International Patent Publication WO 00/46355. |
| 2 | Human histo blood group A transferase cDNA sequence | GenBank Accession J05175 See also Accession Nos. AF134413 & AF134412; Yamamoto et al., Nature May 17 1990; 345: 229 (1990); U.S. Pat. No. 5,326,857 |
| 3 | Human histo blood group A transferase amino acid sequence | (supra) FIG. 3 |
| 4 | Human histo blood group B transferase cDNA sequence | GenBank Accession AF134414 Yamamoto et al., Nature May 17 1990; 345: 229 (1990); U.S. Pat. No. 5,326,857 |
| 5 | Human histo blood group B transferase amino acid sequence | (supra) FIG. 3 |
| 6 | Marmoset α1,3-galactosyltransferase amino acid sequence | GenBank Accession S71333 Henion et al., Glycobiology 4,193 (1994) FIG. 3 |
| 7 | Amino acid translation of human 1,3-galactosyltransferase pseudogene | (infra) FIG. 3 |
| 8 | Sheep α1,3-galactosyltransferase amino acid sequence | Chris Denning & John Clark, Geron Biomed FIG. 3 |
| 9 | Bovine α1,3-galactosyltransferase amino acid sequence | GenBank Accession J04989 Joziasse et al. "Bovine α1->3-galactosyltransferase" J. Biol. Chem. 264, 14290 (1989) FIG. 3 |
| 10 | Pig α1,3-galactosyltransferase amino acid sequence | GenBank Accession L36152 Sus scrofa alpha-1,3-galactosyltransferase mRNA. Strahan et al. "cDNA sequence and chromosome localization of pig α1,3 galactosyltransferase" Immunogenetics 41, 101 (1995) See also GenBank Accession L36535 Sandrin et al. "Characterization of cDNA clones for porcine a(1,3)galactosyl transferase" Xenotransplantation (1994) FIG. 3 |
| 11 | Mouse α1,3-galactosyltransferase amino acid sequence | GenBank Accession M26925 Larsen et al. "Isolation of a cDNA encoding a murine UDP galactose: β-D-galactosyl-1,4-N-acetyl-D-glucosaminide alpha-1,3-galactosyltransferase" Proc. Natl. Acad. |

TABLE 2-continued

Sequences listed in this Disclosure

| SEQ. ID NO: | Designation | Reference |
|---|---|---|
| | | Sci. USA 86, 8227 (1989)<br>See also GenBank Accession IM85153<br>Joziasse et al. "Murine alpha-1,3-<br>galactosyltransferase: A single gene locus<br>specifies four isoforms of the enzyme by<br>alternative splicing" J. Biol. Chem. 267,<br>5534 (1992)<br>FIG. 3 |
| 12 | Consensus α1,3-galactosyltransferase<br>amino acid sequence | This Invention<br>FIG. 3 |
| 13 | Humanized α1,3-galactosyltransferase<br>amino acid sequence | This Invention<br>FIG. 3 |
| 14 | Marmoset α1,3-galactosyltransferase<br>cDNA sequence | GenBank Accession S71333<br>Henion et al., Glycobiology 4,193 (1994)<br>FIG. 4 |
| 15 | Human α1,3-galactosyltransferase<br>pseudogene sequence | GenBank Accession J05421<br>Larsen et al., J. Biol. Chem. .265: 7055,<br>1990<br>See also GenBank Accession M60263<br>Joziasse et al. "Characterization of an<br>alpha-1->3-galactosyltransferase<br>homologue on human chromosome 12 that<br>is organized as a processed pseudogene"<br>J. Biol. Chem. 266, 6991 (1991)<br>FIG. 4 |
| 16 | Humanized α1,3-galactosyltransferase<br>encoding sequence | This Invention<br>FIG. 4 |
| 17 | Sheep α1,3-galactosyltransferase<br>encoding sequence | Chris Denning & John Clark, Geron Biomed |

What is claimed as the invention is:

1. An isolated polynucleotide encoding SEQ. ID NOs:12, SEQ. ID NO:13, or a fragment of SEQ. ID NO:13, wherein said fragment has glycosyltransferase activity, under control of a telomerase transcriptional control element.

2. An isolated polynucleotide comprising an encoding sequence for a humanized or consensus α(1,3) galactosyltransferase, comprising the amino acid sequence shown in SEQ. ID NO:12, SEQ. ID NO:13, or a fragment of SEQ. ID NO:13, wherein said fragment has glycosyltransferase activity.

3. The polynucleotide of claim 2, encoding the amino acid sequence shown in SEQ. ID NO:12.

4. The polynucleotide of claim 2, encoding the amino acid sequence shown in SEQ. ID NO:13, or a fragment of SEQ. ID NO:13, wherein said fragment has glycosyltranaferase activity.

5. The polynucleotide of claim 2, wherein the encoding sequence is operatively linked to a transcriptional control element.

6. The polynucleotide of claim 5, wherein the transcriptional control element is a telomerase promoter.

7. The polynucleotide of claim 6, wherein the promoter comprises at least 25 consecutive nucleotides in SEQ. ID NO:1.

8. The polynucleotide of claim 2, contained in a viral vector.

9. The polynucleotide of claim 2, contained in an adenovirus vector.

10. A human cell containing the polynucleotide of claim 2.

* * * * *

SEQUENCE LISTING

<160> NUMBER OF SEQ ID NOS: 17

<210> SEQ ID NO 1
<211> LENGTH: 15418
<212> TYPE: DNA
<213> ORGANISM: Homo sapiens

<400> SEQUENCE: 1

```
gcggccgcga gctctaatac gactcactat agggcgtcga ctcgatcaat ggaagatgag    60
gcattgccga agaaaagatt aatggatttg aacacacagc aacagaaact acatgaagtg   120
aaacacagga aaaaaaagat aaagaaacga aagaaaagg gcatcagtga gcttcagcag   180
aagttccatc ggccttacat atgtgtaagc agaggccctg taggagcaga ggcaggggga   240
aaatacttta agaaataatg tctaaaagtt tttcaaatat gaggaaaaac ataaaaccac   300
agatccaaga agctcaacaa aacaaagcac aagaaacagg aagaaattaa aagttatatc   360
acagtcaaat tgctgaaaac cagcaacaaa gagaatatct taagagtatc agaggaaaag   420
agattaatga caggccaaga aacaatgaaa acaatacaga tttcttgtag gaaacacaag   480
acaaaagaca ttttttaaaa ccaaaaggaa aaaaaatgct acattaaaat gtttttttacc   540 cactgaaagt atatttcaaa acatattta ggccaggctt ggtggctcac acctgtaatc   600
ccagcacttt gggaggccaa ggtgggtgga tcgcttaagg tcaggagttc gagaccagcc   660
tggccaatat agcgaaaccc catctgtact aaaaacacaa aaattagctg ggtgtggtga   720
cacatgcctg taatcccagg tactcaggag gctaaggcag gagaattgct tgaactggga   780
ggcagaggtg gtgagccaag attgcaccag tgcactccag ccttggtgac agagtgaaac   840
```

-continued

```
tccatctcaa aaacaaacaa acaaaataca tatacataaa tatatatgca catatatata        900
catatataaa tatatataca catatataaa tctatataca tatatacata tatacacata        960
tataaatcta tatacatata tatacatata taatatattt acatatataa atatatacat       1020
atataaatat acatatataa atacatatat aaatatacat atataaatat acatatataa       1080
atatacatat ataaatatat acatatataa atatacatat ataaatatat atacatatat       1140
aaatatataa atatacaagt atatacaaat atatacatat ataaatgtat atacgtatat       1200
acatatatat ataaatatat aaaaaaactt ttggctgggc acctttccaa atctcatggc       1260
acatataagt ctcatggtaa cctcaaataa aaaaacatat aacagataca ccaaaaataa       1320
aaaccaataa attaaatcat gccaccagaa gaaattacct tcactaaaag gaacacagga       1380
aggaaagaaa gaaggaagag aagaccatga aacaaccaga aaacaaacaa caaaacagca       1440
ggagtaattc ctgacttatc aataataatg ctgggtgtaa atggactaaa ctctccaatc       1500
aaaagacata gagtggctga atggacgaaa aaaacaagac tcaataatct gttgcctaca       1560
agaatatact tcacctataa agggacacat agactgaaaa taaaaggaag gaaaaatatt       1620
ctatgcaaat ggaaaccaaa aaaagaacag aactagctac acttatatca gacaaaatag       1680
atttcaagac aaaaagtaca aaaagagaca aagtaattat ataataataa agcaaaaaga       1740
tataacaatt gtgaatttat atgcgcccaa cactgggaca cccagatata tacagcaaat       1800
attattagaa ctaaggagag agagagatcc ccatacaata atagctggag acttcaccccc       1860
gcttttagca ttgacagat catccagaca gaaaatcaac caaaaaattg gacttaatct        1920
ataatataga acaaatgtac ctaattgatg tttacaagac atttcatcca gtagttgcag       1980
aatatgcatt ttttcctcag catatggatc attctcaagg atagaccata tattaggcca       2040
cagaacaagc cattaaaaat tcaaaaaaat tgagccaggc atgatggctt atgcttgtaa       2100
ttacagcact ttggggaggg tgaggtggga ggatgtcttg agtacaggag tttgagacca       2160
gcctgggcaa aatagtgaga ccctgtctct acaaactttt tttttaatt agccaggcat        2220
agtggtgtgt gcctgtagtc ccagctactt aggaggctga agtgggagga tcacttgagc       2280
ccaagagttc aaggctacgg tgagccatga ttgcaacacc acacaccagc cttggtgaca       2340
gaatgagacc ctgtctcaaa aaaaaaaaaa aaaattgaaa taatataaag catcttctct       2400
ggccacagtg gaacaaaacc agaaatcaac aacaagagga attttgaaaa ctatacaaac       2460
acatgaaaat taaacaatat acttctgaat aaccagtgag tcaatgaaga aattaaaaag       2520
gaaattgaaa aatttatttta agcaaatgat aacggaaaca taacctctca aaacccacgg     2580
tatacagcaa aagcagtgct aagaaggaag tttatagcta taagcagcta catcaaaaaa       2640
gtagaaaagc caggcgcagt ggctcatgcc tgtaatccca gcactttggg aggccaaggc       2700
gggcagatcg cctgaggtca ggagttcgag accagcctga ccaacacaga gaaaccttgt      2760
cgctactaaa aatacaaaat tagctgggca tggtggcaca tgcctgtaat cccagctact       2820
cgggaggctg aggcaggata accgcttgaa cccaggaggt ggaggttgcg gtgagccggg       2880
attgcgccat tggactccag cctgggtaac aagagtgaaa ccctgtctca agaaaaaaaa       2940
aaaagtagaa aaacttaaaa atacaaccta atgatgcacc ttaaagaact agaaaagcaa       3000
gagcaaacta aacctaaaat tggtaaaaga aagaaaataa taaagatcag agcagaaata       3060
aatgaaactg aaagataaca atacaaaaga tcaacaaaat taaagttgg tttttttgaaa      3120
agataaacaa aattgacaaa cctttgccca gactaagaaa aaggaaaga agacctaaat        3180
aaataaagtc agagatgaaa aaagagacat tacaactgat accacagaaa ttcaaggat        3240
```

```
cactagaggc tactatgagc aactgtacac taataaattg aaaaacctag aaaaaataga   3300
taaattccta gatgcataca acctaccaag attgaaccat gaagaaatcc aaagcccaaa   3360
cagaccaata acaataatgg gattaaagcc ataataaaaa gtctcctagc aaagagaagc   3420
ccaggaccca atggcttccc tgctggattt taccaatcat ttaaagaaga atgaattcca   3480
atcctactca aactattctg aaaaatagag gaaagaatac ttccaaactc attctacatg   3540
gccagtatta ccctgattcc aaaaccagac aaaaacacat caaaaacaaa caaacaaaaa   3600
aacagaaaga aagaaaacta caggccaata tccctgatga atactgatac aaaaatcctc   3660
aacaaaacac tagcaaacca aattaaacaa caccttcgaa agatcattca ttgtgatcaa   3720
gtgggatttta ttccagggat ggaaggatgg ttcaacatat gcaaatcaat caatgtgata   3780
catcatccca acaaaatgaa gtacaaaaac tatatgatta tttcacttta tgcagaaaaa   3840
gcatttgata aaattctgca cccttcatga taaaaaccct caaaaaacca ggtatacaag   3900
aaacatacag gccaggcaca gtggctcaca cctgcgatcc cagcactctg ggaggccaag   3960
gtgggatgat tgcttgggcc caggagtttg agactagcct gggcaacaaa atgagacctg   4020
gtctacaaaa aactttttta aaaaattagc caggcatgat ggcatatgcc tgtagtccca   4080
gctagtctgg aggctgaggt gggagaatca cttaagccta ggaggtcgag gctgcagtga   4140
gccatgaaca tgtcactgta ctccagccta gacaacagaa caagaccccca ctgaataaga   4200
agaaggagaa ggagaaggga gaaggagggg agaagggagg aggaggagaa ggaggaggtg   4260
gaggagaagt ggaaggggaa ggggaaggga aagaggaaga agaagaaaca tatttcaaca   4320
taataaaagc cctatatgac agaccgaggt agtattatga ggaaaaactg aaagcctttc   4380
ctctaagatc tggaaaatga caagggccca ctttcaccac tgtgattcaa catagtacta   4440
gaagtcctag ctagagcaat cagataagag aaagaaataa aaggcatcca aactggaaag   4500
gaagaagtca aattatcctg tttgcagatg atatgatctt atatctggaa aagacttaag   4560
acaccactaa aaaactatta gagctgaaat ttggtacagc aggatacaaa atcaatgtac   4620
aaaaatcagt agtatttcta tattccaaca gcaaacaatc tgaaaagaa accaaaaaag   4680
cagctacaaa taaaattaaa cagctaggaa ttaaccaaag aagtgaaaga tctctacaat   4740
gaaaactata aaatattgat aaaagaaatt gaagagggca caaaaaaaga aaagatattc   4800
catgttcata gattggaaga ataaatactg ttaaaatgtc catactaccc aaagcaattt   4860
acaaattcaa tgcaatccct attaaaatac taatgacgtt cttcacagaa atagaagaaa   4920
caattctaag atttgtacag aaccacaaaa gacccagaat agccaaagct atcctgacca   4980
aaaagaacaa aactggaagc atcacattac ctgacttcaa attatactac aaagctatag   5040
taacccaaac tacatggtac tggcataaaa acagatgaga catggaccag aggaacagaa   5100
tagagaatcc agaaacaaat ccatgcatct acagtgaact cattttgac aaaggtgcca   5160
agaacatact ttggggaaaa gataatctct tcaataaatg gtgctggagg aactggatat   5220
ccatatgcaa aataacaata ctagaactct gtctctcacc atatacaaaa gcaaatcaaa   5280
atggatgaaa ggcttaaatc taaaacctca aactttgcaa ctactaaaag aaaacaccgg   5340
agaaactctc caggacattg gagtgggcaa agacttcttg agtaattccc tgcaggcaca   5400
ggcaaccaaa gcaaaaacag acaaatggga tcatatcaag ttaaaaagct tctgcccagc   5460
aaaggaaaca atcaacaaag agaagagaca acccacagaa tggagaataa tatttgcaaa   5520
ctattcatct aacaaggaat taataaccag tatatataag gagctcaaac tactctataa   5580
```

-continued

```
gaaaaacacc taataagctg attttcaaaa ataagcaaaa gatctgggta gacatttctc    5640
aaaataagtc atacaaatgg caaacaggca tctgaaaatg tgctcaacac cactgatcat    5700
cagagaaatg caaatcaaaa ctactatgag agatcatctc accccagtta aaatggcttt    5760
tattcaaaag acaggcaata acaaatgcca gtgaggatgt ggataaaagg aaacccttgg    5820
acactgttgg tgggaatgga aattgctacc actatggaga acagtttgaa agttcctcaa    5880
aaaactaaaa ataaagctac catacagcaa tcccattgct aggtatatac tccaaaaaag    5940
ggaatcagtg tatcaacaag ctatctccac tcccacattt actgcagcac tgttcatagc    6000
agccaaggtt tggaagcaac ctcagtgtcc atcaacagac gaatggaaaa agaaaatgtg    6060
gtgcacatac acaatggagt actacgcagc cataaaaaag aatgagatcc tgtcagttgc    6120
aacagcatgg ggggcactgg tcagtatgtt aagtgaaata agccaggcac agaaagacaa    6180
acttttcatg ttctccctta cttgtgggag caaaaattaa acaattgac atagaaatag    6240 aggagaatgg tggttctaga ggggtggggg acaggtgac tagagtcaac aataatttat    6300
tgtatgtttt aaaataacta aaagagtata attgggttgt ttgtaacaca agaaaggat    6360 aaatgcttga aggtgacaga taccccattt accctgatgt gattattaca cattgtatgc    6420
ctgtatcaaa atatctcatg tatgctatag atataaaccc tactatatta aaaattaaaa    6480
ttttaatggc caggcacggt ggctcatgtc cataatccca gcactttggg aggccgaggc    6540
ggtggatcac ctgaggtcag gagtttgaaa ccagtctggc caccatgatg aaaccctgtc    6600
tctactaaag atacaaaaat tagccaggcg tggtggcaca tacctgtagt cccaactact    6660
caggaggctg agacaggaga attgcttgaa cctgggaggc ggaggttgca gtgagccgag    6720
atcatgccac tgcactgcag cctgggtgac agagcaagac tccatctcaa aacaaaaaca    6780 aaaaaagaa gattaaaatt gtaattttta tgtaccgtat aaatatatac tctactatat    6840
tagaagttaa aaattaaaac aattataaaa ggtaattaac cacttaatct aaaataagaa    6900
caatgtatgt gggggtttcta gcttctgaag aagtaaaagt tatggccacg atggcagaaa    6960
tgtgaggagg aacagtggaa agttactgtt gttagacgct catactctct gtaagtgact    7020
taattttaac caaagacagg ctgggagaag ttaaagaggc attctataag ccctaaaaca    7080
actgctaata atggtgaaag gtaatctcta ttaattacca ataattacag atatctctaa    7140
aatcgagctg cagaattggc acgtctgatc acaccgtcct ctcattcacg gtgctttttt    7200
tcttgtgtgc ttggagattt tcgattgtgt gttcgtgttt ggttaaactt aatctgtatg    7260
aatcctgaaa cgaaaaatgg tggtgatttc ctccagaaga attagagtac ctggcaggaa    7320
gcaggtggct ctgtggacct gagccacttc aatcttcaag ggtctctggc caagacccag    7380
gtgcaaggca gaggcctgat gacccgagga caggaaagct cggatgggaa ggggcgatga    7440
gaagcctgcc tcgttggtga gcagcgcatg aagtgcccct atttacgctt tgcaaagatt    7500
gctctggata ccatctggaa aaggcggcca gcgggaatgc aaggagtcag aagcctcctg    7560
ctcaaaccca ggccagcagc tatggcgccc acccgggcgt gtgccagagg gagaggagtc    7620
aaggcacctc gaagtatggc ttaaatcttt ttttcacctg aagcagtgac caaggtgtat    7680
tctgagggaa gcttgagtta ggtgccttct ttaaaacaga aagtcatgga agcacccttc    7740
tcaagggaaa accagacgcc cgctctgcgg tcatttacct ctttcctctc tccctctctt    7800
gccctcgcgg tttctgatcg ggacagagtg accccgtgg agcttctccg agcccgtgct    7860
gaggaccctc ttgcaaaggg ctccacagac ccccgccctg gagagaggag tctgagcctg    7920
gcttaataac aaactgggat gtggctgggg gcggacagcg acggcgggat tcaaagactt    7980
```

```
aattccatga gtaaattcaa cctttccaca tccgaatgga tttggatttt atcttaatat    8040
tttcttaaat ttcatcaaat aacattcagg agtgcagaaa tccaaaggcg taaaacagga    8100
actgagctat gtttgccaag gtccaaggac ttaataacca tgttcagagg gattttttcgc   8160
cctaagtact tttttattggt tttcataagg tggcttaggg tgcaagggaa agtacacgag   8220
gagaggactg ggcggcaggg ctatgagcac ggcaaggcca ccggggagag agtccccggc    8280
ctgggaggct gacagcagga ccactgaccg tcctccctgg gagctgccac attgggcaac    8340
gcgaaggcgg ccacgctgcg tgtgactcag gaccccatac cggcttcctg ggcccaccca    8400
cactaaccca ggaagtcacg gagctctgaa cccgtggaaa cgaacatgac ccttgcctgc    8460
ctgcttccct gggtgggtca agggtaatga agtggtgtgc aggaaatggc catgtaaatt    8520
acacgactct gctgatgggg accgttcctt ccatcattat tcatcttcac ccccaaggac    8580
tgaatgattc cagcaacttc ttcgggtgtg acaagccatg acaacactca gtacaaaac    8640
cactctttta ctaggcccac agagcacggc ccacacccct gatatattaa gagtccagga   8700
gagatgaggc tgctttcagc caccaggctg gggtgacaac agcggctgaa cagtctgttc    8760
ctctagacta gtagaccctg gcaggcactc ccccagattc tagggcctgg ttgctgcttc    8820
ccgagggcgc catctgccct ggagactcag cctggggtgc cacactgagg ccagccctgt    8880
ctccacaccc tccgcctcca ggcctcagct tctccagcag cttcctaaac cctgggtggg    8940
ccgtgttcca gcgctactgt ctcacctgtc ccactgtgtc ttgtctcagc gacgtagctc    9000
gcacggttcc tcctcacatg gggtgtctgt ctccttcccc aacactcaca tgcgttgaag    9060
ggaggagatt ctgcgcctcc cagactggcc cctctgagcc tgaacctggc tcgtggcccc    9120
cgatgcaggt tcctggcgtc cggctgcacg ctgacctcca tttccaggcg ctccccgtct    9180
cctgtcatct gccggggcct gccggtgtgt tcttctgttt ctgtgctcct ttccacgtcc    9240
agctgcgtgt gtctctgtcc gctagggtct cggggttttt ataggcatag gacggggggcg   9300
tggtgggcca gggcgctctt gggaaatgca acatttgggt gtgaaagtag gagtgcctgt    9360
cctcacctag gtccacgggc acaggcctgg ggatggagcc cccgccaggg acccgccctt    9420
ctctgcccag cacttttctg cccccctccc tctggaacac agagtggcag tttccacaag    9480
cactaagcat cctcttccca aaagacccag cattggcacc cctggacatt tgccccacag    9540
ccctgggaat tcacgtgact acgcacatca tgtacacact cccgtccacg accgaccccc    9600
gctgttttat tttaatagct acaaagcagg gaaatccctg ctaaaatgtc ctttaacaaa    9660
ctggttaaac aaacgggtcc atccgcacgg tggacagttc ctcacagtga agaggaacat    9720
gccgtttata aagcctgcag gcatctcaag ggaattacgc tgagtcaaaa ctgccacctc    9780
catgggatac gtacgcaaca tgctcaaaaa gaaagaattt caccccatgg caggggagtg    9840
gttgggggt taaggacggt gggggcagca gctgggggct actgcacgca ccttttacta     9900
aagccagttt cctggttctg atggtattgg ctcagttatg ggagactaac cataggggag    9960
tggggatggg ggaaccccgga ggctgtgcca tctttgccat gcccgagtgt cctgggcagg   10020
ataatgctct agagatgccc acgtcctgat tcccccaaac ctgtggacag aacccgcccg    10080
gccccagggc ctttgcaggt gtgatctccg tgaggaccct gaggtctggg atccttcggg   10140
actacctgca ggcccgaaaa gtaatccagg ggttctggga agaggcgggc aggagggtca   10200
gagggggggca gcctcaggac gatggaggca gtcagtctga ggctgaaaag ggaggggaggg  10260
cctcgagccc aggcctgcaa gcgcctccag aagctggaaa aagcggggaa gggacccctcc  10320
```

-continued

```
acggagcctg cagcaggaag gcacggctgg cccttagccc accagggccc atcgtggacc    10380
tccggcctcc gtgccatagg agggcactcg cgctgccctt ctagcatgaa gtgtgtgggg    10440
atttgcagaa gcaacaggaa acccatgcac tgtgaatcta ggattatttc aaaacaaagg    10500
tttacagaaa catccaagga cagggctgaa gtgcctccgg gcaagggcag ggcaggcacg    10560
agtgatttta tttagctatt ttattttatt tacttacttt ctgagacaga gttatgctct    10620
tgttgcccag gctggagtgc agcggcatga tcttggctca ctgcaacctc cgtctcctgg    10680
gttcaagcaa ttctcgtgcc tcagcctccc aagtagctgg gatttcaggc gtgcaccacc    10740
acacccggct aattttgtat ttttagtaga gatgggcttt caccatgttg gtcaggctga    10800
tctcaaaatc ctgacctcag gtgatccgcc cacctcagcc tcccaaagtg ctgggattac    10860
aggcatgagc cactgcacct ggcctattta accattttaa aacttccctg gctcaagtc    10920
acacccactg gtaaggagtt catggagttc aatttcccct ttactcagga gttaccctcc    10980
tttgatattt tctgtaattc ttcgtagact ggggatacac cgtctcttga catattcaca    11040
gtttctgtga ccacctgtta tcccatggga cccactgcag gggcagctgg gaggctgcag    11100
gcttcaggtc ccagtggggt tgccatctgc cagtagaaac ctgatgtaga atcagggcgc    11160
gagtgtggac actgtcctga atctcaatgt ctcagtgtgt gctgaaacat gtagaaatta    11220
aagtccatcc ctcctactct actgggattg agccccttcc ctatcccccc ccaggggcag    11280
aggagttcct ctcactcctg tggaggaagg aatgatactt tgttattttt cactgctggt    11340
actgaatcca ctgtttcatt tgttggtttg tttgttttgt tttgagaggc ggtttcactc    11400
ttgttgctca ggctggaggg agtgcaatgg cgcgatcttg gcttactgca gcctctgcct    11460
cccaggttca agtgattctc ctgcttccgc ctcccatttg gctgggatta caggcacccg    11520
ccaccatgcc cagctaattt tttgtatttt tagtagagac gggggtgggg gtggggttca    11580
ccatgttggc caggctggtc tcgaacttct gacctcagat gatccacctg cctctgcctc    11640
ctaaagtgct gggattacag gtgtgagcca ccatgcccag ctcagaattt actctgttta    11700
gaaacatctg ggtctgaggt aggaagctca ccccactcaa gtgttgtggt gtttaagcc    11760
aatgatagaa tttttttatt gttgttagaa cactcttgat gttttacact gtgatgacta    11820
agacatcatc agcttttcaa agacacacta actgcaccca taatactggg gtgtcttctg    11880
ggtatcagcg atcttcattg aatgccggga ggcgtttcct cgccatgcac atggtgttaa    11940
ttactccagc ataatcttct gcttccattt cttctcttcc ctcttttaaa attgtgtttt    12000
ctatgttggc ttctctgcag agaaccagtg taagctacaa cttaactttt gttggaacaa    12060
attttccaaa ccgccccttt gcccagtggg cagagacaat tcacaaacac agccctttaa    12120
aaaggcttag ggatcactaa ggggatttct agaagagcga cccgtaatcc taagtattta    12180
caagacgagg ctaacctcca gcgagcgtga cagcccaggg agggtgcgag gcctgttcaa    12240
atgctagctc cataaataaa gcaatttcct ccggcagttt ctgaaagtag gaaaggttac    12300
atttaaggtt cgctttgtta gcatttcagt gttttgccgac ctcagctaca gcatccctgc    12360
aaggcctcgg gagacccaga gtttctcgc cccttagatc caaacttgag caacccggag    12420
tctggattcc tgggaagtcc tcagctgtcc tgcggttgtg ccggggcccc aggtctggag    12480
gggaccagtg gccgtgtggc ttctactgct gggctggaag tcgggcctcc tagctctgca    12540
gtccgaggct tggagccagg tgcctggacc ccgaggctgc cctccaccct gtgcgggcgg    12600
gatgtgacca gatgttggcc tcatctgcca gacagagtgc cggggcccag ggtcaaggcc    12660
gttgtggctg gtgtgaggcg cccggtgcgc ggccagcagg agcgcctggc tccatttccc    12720
```

-continued

```
acccttctc gacgggaccg ccccggtggg tgattaacag atttggggtg gtttgctcat    12780
ggtggggacc cctcgccgcc tgagaacctg caaagagaaa tgacgggcct gtgtcaagga    12840
gcccaagtcg cggggaagtg ttgcagggag gcactccggg aggtcccgcg tgcccgtcca    12900
gggagcaatg cgtcctcggg ttcgtcccca gccgcgtcta cgcgcctccg tcctcccctt    12960
cacgtccggc attcgtggtg cccggagccc gacgccccgc gtccggacct ggaggcagcc    13020
ctgggtctcc ggatcaggcc agcggccaaa gggtcgccgc acgcacctgt tcccagggcc    13080
tccacatcat ggcccctccc tcgggttacc ccacagccta ggccgattcg acctctctcc    13140
gctggggccc tcgctggcgt ccctgcaccc tgggagcgcg agcggcgcgc gggcggggaa    13200
gcgcggccca ccccgggg tccgcccgga gcagctgcgc tgtcggggcc aggccgggct    13260
cccagtggat tcgcgggcac agacgcccag gaccgcgctt cccacgtggc ggagggactg    13320
gggacccggg caccgtcct gcccttcac cttccagctc cgcctcctcc gcgcggaccc    13380
cgccccgtcc cgaccctcc cgggtccccg gcccagcccc ctccgggccc tccagcccc    13440 tcccttcct ttccgcggcc ccgccctctc ctcgcgcgcg gagtttcagg cagcgctgcg    13500
tcctgctgcg cacgtgggaa gccctggccc cggccacccc cgcgatgccg cgcgctcccc    13560
gctgccgagc cgtgcgctcc ctgctgcgca gccactaccg cgaggtgctg ccgctggcca    13620
cgttcgtgcg gcgcctgggg ccccagggct ggcggctggt gcagcgcggg gacccggcgg    13680 cttccgcgc gctggtggcc cagtgcctgg tgtgcgtgcc ctgggacgca cggccgcccc    13740
ccgccgcccc ctccttccgc caggtgggcc tccccgggt cggcgtccgg ctggggttga    13800
gggcggccgg ggggaaccag cgacatgcgg agagcagcgc aggcgactca gggcgcttcc    13860
cccgcaggtg tcctgcctga aggagctggt ggcccgagtg ctgcagaggc tgtgcgagcg    13920
cggcgcgaag aacgtgctgg ccttcggctt cgcgctgctg gacggggccc gcggggcccc    13980
ccccgaggcc ttcaccacca gcgtgcgcag ctacctgccc aacacggtga ccgacgcact    14040 gcggggagc ggggcgtggg ggctgctgct gcgccgcgtg ggcgacgacg tgctggttca    14100
cctgctggca cgctgcgcgc tctttgtgct ggtggctccc agctgcgcct accaggtgtg    14160
cgggccgccg ctgtaccagc tcggcgctgc cactcaggcc cggccccgc cacacgctag    14220 tggaccccga aggcgtctgg gatgcgaacg ggcctggaac catagcgtca gggaggccgg    14280 ggtcccctg ggcctgccag ccccgggtgc gaggaggcgc gggggcagtg ccagccgaag    14340
tctgccgttg cccaagaggc ccaggcgtgg cgctgcccct gagccggagc ggacgcccgt    14400
tgggcagggg tcctgggccc acccgggcag gacgcgtgga ccgagtgacc gtggtttctg    14460
tgtggtgtca cctgccagac ccgccgaaga agccacctct ttggagggtg cgctctctgg    14520
cacgcgccac tcccacccat ccgtgggccg ccagcaccac gcgggccccc catccacatc    14580
gcggccacca cgtccctggg acacgccttg tccccggtg tacgccgaga ccaagcactt    14640
cctctactcc tcaggcgaca aggagcagct gcggccctcc ttcctactca gctctctgag    14700
gcccagcctg actggcgctc ggaggctcgt ggagaccatc tttctggggtt ccaggccctg    14760 gatgccaggg actccccgca ggttgccccg cctgccccag cgctactggc aaatgcggcc    14820
cctgtttctg gagctgcttg gaaccacgc gcagtgcccc tacggggtgc tcctcaagac    14880
gcactgcccg ctgcgagctg cggtcacccc agcagccggt gtctgtgccc gggagaagcc    14940
ccagggctct gtggcggccc ccgaggagga ggacacagac cccgtcgcc tggtgcagct    15000 gctccgccag cacagcagcc cctggcaggt gtacggcttc gtgcgggcct gcctgcgccg    15060
```

-continued

```
gctggtgccc ccaggcctct ggggctccag gcacaacgaa cgccgcttcc tcaggaacac    15120
caagaagttc atctccctgg ggaagcatgc caagctctcg ctgcaggagc tgacgtggaa    15180
gatgagcgtg cgggactgcg cttggctgcg caggagccca ggtgaggagg tggtggccgt    15240
cgagggccca ggcccagag ctgaatgcag taggggctca gaaaaggggg caggcagagc     15300
cctggtcctc ctgtctccat cgtcacgtgg gcacacgtgg cttttcgctc aggacgtcga    15360
gtggacacgg tgatcgagtc gactcccttt agtgagggtt aattgagctc gcggccgc     15418
```

<210> SEQ ID NO 2
<211> LENGTH: 1062
<212> TYPE: DNA
<213> ORGANISM: Homo sapiens
<220> FEATURE:
<221> NAME/KEY: CDS
<222> LOCATION: (1)..(1062)
<223> OTHER INFORMATION:

<400> SEQUENCE: 2

| | | | | | | | | | | | | | | | | |
|---|---|---|---|---|---|---|---|---|---|---|---|---|---|---|---|---|
| atg | gcc | gag | gtg | ttg | cgg | acg | ctg | gcc | gga | aaa | cca | aaa | tgc | cac | gca | 48 |
| Met | Ala | Glu | Val | Leu | Arg | Thr | Leu | Ala | Gly | Lys | Pro | Lys | Cys | His | Ala | |
| 1 | | | | 5 | | | | | 10 | | | | | 15 | | |

| ctt | cga | cct | atg | atc | ctt | ttc | cta | ata | atg | ctt | gtc | ttg | gtc | ttg | ttt | 96 |
|---|---|---|---|---|---|---|---|---|---|---|---|---|---|---|---|---|
| Leu | Arg | Pro | Met | Ile | Leu | Phe | Leu | Ile | Met | Leu | Val | Leu | Val | Leu | Phe | |
| | | | 20 | | | | | 25 | | | | | 30 | | | |

| ggt | tac | ggg | gtc | cta | agc | ccc | aga | agt | cta | atg | cca | gga | agc | ctg | gaa | 144 |
|---|---|---|---|---|---|---|---|---|---|---|---|---|---|---|---|---|
| Gly | Tyr | Gly | Val | Leu | Ser | Pro | Arg | Ser | Leu | Met | Pro | Gly | Ser | Leu | Glu | |
| | | 35 | | | | | 40 | | | | | 45 | | | | |

| cgg | ggg | ttc | tgc | atg | gct | gtt | agg | gaa | cct | gac | cat | ctg | cag | cgc | gtc | 192 |
|---|---|---|---|---|---|---|---|---|---|---|---|---|---|---|---|---|
| Arg | Gly | Phe | Cys | Met | Ala | Val | Arg | Glu | Pro | Asp | His | Leu | Gln | Arg | Val | |
| 50 | | | | | 55 | | | | | 60 | | | | | | |

| tcg | ttg | cca | agg | atg | gtc | tac | ccc | cag | cca | aag | gtg | ctg | aca | ccg | tgg | 240 |
|---|---|---|---|---|---|---|---|---|---|---|---|---|---|---|---|---|
| Ser | Leu | Pro | Arg | Met | Val | Tyr | Pro | Gln | Pro | Lys | Val | Leu | Thr | Pro | Trp | |
| 65 | | | | | 70 | | | | | 75 | | | | | 80 | |

| aag | gat | gtc | ctc | gtg | gtg | acc | cct | tgg | ctg | gct | ccc | att | gtc | tgg | gag | 288 |
|---|---|---|---|---|---|---|---|---|---|---|---|---|---|---|---|---|
| Lys | Asp | Val | Leu | Val | Val | Thr | Pro | Trp | Leu | Ala | Pro | Ile | Val | Trp | Glu | |
| | | | | 85 | | | | | 90 | | | | | 95 | | |

| ggc | aca | ttc | aac | atc | gac | atc | ctc | aac | gag | cag | ttc | agg | ctc | cag | aac | 336 |
|---|---|---|---|---|---|---|---|---|---|---|---|---|---|---|---|---|
| Gly | Thr | Phe | Asn | Ile | Asp | Ile | Leu | Asn | Glu | Gln | Phe | Arg | Leu | Gln | Asn | |
| | | | 100 | | | | | 105 | | | | | 110 | | | |

| acc | acc | att | ggg | tta | act | gtg | ttt | gcc | atc | aag | aaa | tac | gtg | gct | ttc | 384 |
|---|---|---|---|---|---|---|---|---|---|---|---|---|---|---|---|---|
| Thr | Thr | Ile | Gly | Leu | Thr | Val | Phe | Ala | Ile | Lys | Lys | Tyr | Val | Ala | Phe | |
| | | 115 | | | | | 120 | | | | | 125 | | | | |

| ctg | aag | ctg | ttc | ctg | gag | acg | gcg | gag | aag | cac | ttc | atg | gtg | ggc | cac | 432 |
|---|---|---|---|---|---|---|---|---|---|---|---|---|---|---|---|---|
| Leu | Lys | Leu | Phe | Leu | Glu | Thr | Ala | Glu | Lys | His | Phe | Met | Val | Gly | His | |
| 130 | | | | | 135 | | | | | 140 | | | | | | |

| cgt | gtc | cac | tac | tat | gtc | ttc | acc | gac | cag | ctg | gcc | gcg | gtg | ccc | cgc | 480 |
|---|---|---|---|---|---|---|---|---|---|---|---|---|---|---|---|---|
| Arg | Val | His | Tyr | Tyr | Val | Phe | Thr | Asp | Gln | Leu | Ala | Ala | Val | Pro | Arg | |
| 145 | | | | | 150 | | | | | 155 | | | | | 160 | |

| gtg | acg | ctg | ggg | acc | ggt | cgg | cag | ctg | tca | gtg | ctg | gag | gtg | cgc | gcc | 528 |
|---|---|---|---|---|---|---|---|---|---|---|---|---|---|---|---|---|
| Val | Thr | Leu | Gly | Thr | Gly | Arg | Gln | Leu | Ser | Val | Leu | Glu | Val | Arg | Ala | |
| | | | | 165 | | | | | 170 | | | | | 175 | | |

| tac | aag | cgc | tgg | cag | gac | gtg | tcc | atg | cgc | cgc | atg | gag | atg | atc | agt | 576 |
|---|---|---|---|---|---|---|---|---|---|---|---|---|---|---|---|---|
| Tyr | Lys | Arg | Trp | Gln | Asp | Val | Ser | Met | Arg | Arg | Met | Glu | Met | Ile | Ser | |
| | | | 180 | | | | | 185 | | | | | 190 | | | |

| gac | ttc | tgc | gag | cgg | cgc | ttc | ctc | agc | gag | gtg | gat | tac | ctg | gtg | tgc | 624 |
|---|---|---|---|---|---|---|---|---|---|---|---|---|---|---|---|---|
| Asp | Phe | Cys | Glu | Arg | Arg | Phe | Leu | Ser | Glu | Val | Asp | Tyr | Leu | Val | Cys | |
| | | 195 | | | | | 200 | | | | | 205 | | | | |

| gtg | gac | gtg | gac | atg | gag | ttc | cgc | gac | cac | gtg | ggc | gtg | gag | atc | ctg | 672 |
|---|---|---|---|---|---|---|---|---|---|---|---|---|---|---|---|---|
| Val | Asp | Val | Asp | Met | Glu | Phe | Arg | Asp | His | Val | Gly | Val | Glu | Ile | Leu | |
| | 210 | | | | | 215 | | | | | 220 | | | | | |

```
act ccg ctg ttc ggc acc ctg cac ccc ggc ttc tac gga agc agc cgg    720
Thr Pro Leu Phe Gly Thr Leu His Pro Gly Phe Tyr Gly Ser Ser Arg
225                 230                 235                 240 gag gcc ttc acc tac gag cgc cgg ccc cag tcc cag gcc tac atc ccc    768
Glu Ala Phe Thr Tyr Glu Arg Arg Pro Gln Ser Gln Ala Tyr Ile Pro
                245                 250                 255 aag gac gag ggc gat ttc tac tac ctg ggg ggg ttc ttc ggg ggg tcg    816
Lys Asp Glu Gly Asp Phe Tyr Tyr Leu Gly Gly Phe Phe Gly Gly Ser
            260                 265                 270 gtg caa gag gtg cag cgg ctc acc agg gcc tgc cac cag gcc atg atg    864
Val Gln Glu Val Gln Arg Leu Thr Arg Ala Cys His Gln Ala Met Met
        275                 280                 285 gtc gac cag gcc aac ggc atc gag gcc gtg tgg cac gac gag agc cac    912
Val Asp Gln Ala Asn Gly Ile Glu Ala Val Trp His Asp Glu Ser His
    290                 295                 300 ctg aac aag tac ctg ctg cgc cac aaa ccc acc aag gtg ctc tcc ccc    960
Leu Asn Lys Tyr Leu Leu Arg His Lys Pro Thr Lys Val Leu Ser Pro
305                 310                 315                 320 gag tac ttg tgg gac cag cag ctg ctg ggc tgg ccc gcc gtc ctg agg   1008
Glu Tyr Leu Trp Asp Gln Gln Leu Leu Gly Trp Pro Ala Val Leu Arg
                325                 330                 335 aag ctg agg ttc act gcg gtg ccc aag aac cac cag gcg gtc cgg aac   1056
Lys Leu Arg Phe Thr Ala Val Pro Lys Asn His Gln Ala Val Arg Asn
            340                 345                 350 ccg tga                                                            1062
Pro

<210> SEQ ID NO 3
<211> LENGTH: 353
<212> TYPE: PRT
<213> ORGANISM: Homo sapiens

<400> SEQUENCE: 3

Met Ala Glu Val Leu Arg Thr Leu Ala Gly Lys Pro Lys Cys His Ala
1               5                   10                  15

Leu Arg Pro Met Ile Leu Phe Leu Ile Met Leu Val Leu Val Leu Phe
            20                  25                  30

Gly Tyr Gly Val Leu Ser Pro Arg Ser Leu Met Pro Gly Ser Leu Glu
        35                  40                  45

Arg Gly Phe Cys Met Ala Val Arg Glu Pro Asp His Leu Gln Arg Val
    50                  55                  60

Ser Leu Pro Arg Met Val Tyr Pro Gln Pro Lys Val Leu Thr Pro Trp
65                  70                  75                  80

Lys Asp Val Leu Val Thr Pro Trp Leu Ala Pro Ile Val Trp Glu
            85                  90                  95

Gly Thr Phe Asn Ile Asp Ile Leu Asn Glu Gln Phe Arg Leu Gln Asn
            100                 105                 110

Thr Thr Ile Gly Leu Thr Val Phe Ala Ile Lys Lys Tyr Val Ala Phe
        115                 120                 125

Leu Lys Leu Phe Leu Glu Thr Ala Glu Lys His Phe Met Val Gly His
    130                 135                 140

Arg Val His Tyr Tyr Val Phe Thr Asp Gln Leu Ala Ala Val Pro Arg
145                 150                 155                 160

Val Thr Leu Gly Thr Gly Arg Gln Leu Ser Val Leu Glu Val Arg Ala
            165                 170                 175

Tyr Lys Arg Trp Gln Asp Val Ser Met Arg Arg Met Glu Met Ile Ser
        180                 185                 190
```

```
Asp Phe Cys Glu Arg Arg Phe Leu Ser Glu Val Asp Tyr Leu Val Cys
            195                 200                 205
Val Asp Val Asp Met Glu Phe Arg Asp His Val Gly Val Glu Ile Leu
210                 215                 220
Thr Pro Leu Phe Gly Thr Leu His Pro Gly Phe Tyr Gly Ser Ser Arg
225                 230                 235                 240
Glu Ala Phe Thr Tyr Glu Arg Arg Pro Gln Ser Gln Ala Tyr Ile Pro
                245                 250                 255
Lys Asp Glu Gly Asp Phe Tyr Tyr Leu Gly Gly Phe Phe Gly Gly Ser
            260                 265                 270
Val Gln Glu Val Gln Arg Leu Thr Arg Ala Cys His Gln Ala Met Met
        275                 280                 285
Val Asp Gln Ala Asn Gly Ile Glu Ala Val Trp His Asp Glu Ser His
    290                 295                 300
Leu Asn Lys Tyr Leu Leu Arg His Lys Pro Thr Lys Val Leu Ser Pro
305                 310                 315                 320
Glu Tyr Leu Trp Asp Gln Gln Leu Leu Gly Trp Pro Ala Val Leu Arg
                325                 330                 335
Lys Leu Arg Phe Thr Ala Val Pro Lys Asn His Gln Ala Val Arg Asn
            340                 345                 350
Pro
```

<210> SEQ ID NO 4
<211> LENGTH: 1065
<212> TYPE: DNA
<213> ORGANISM: Homo sapiens
<220> FEATURE:
<221> NAME/KEY: CDS
<222> LOCATION: (1)..(1065)
<223> OTHER INFORMATION:

<400> SEQUENCE: 4

```
atg gcc gag gtg ttg cgg acg ctg gcc gga aaa cca aaa tgc cac gca        48
Met Ala Glu Val Leu Arg Thr Leu Ala Gly Lys Pro Lys Cys His Ala
1               5                   10                  15 ctt cga cct atg atc ctt ttc cta ata atg ctt gtc ttg gtc ttg ttt       96
Leu Arg Pro Met Ile Leu Phe Leu Ile Met Leu Val Leu Val Leu Phe
                20                  25                  30 ggt tac ggg gtc cta agc ccc aga agt cta atg cca gga agc ctg gaa      144
Gly Tyr Gly Val Leu Ser Pro Arg Ser Leu Met Pro Gly Ser Leu Glu
            35                  40                  45 cgg ggg ttc tgc atg gct gtt agg gaa cct gac cat ctg cag cgc gtc      192
Arg Gly Phe Cys Met Ala Val Arg Glu Pro Asp His Leu Gln Arg Val
        50                  55                  60 tcg ttg cca agg atg gtc tac ccc cag cca aag gtg ctg aca ccg tgt      240
Ser Leu Pro Arg Met Val Tyr Pro Gln Pro Lys Val Leu Thr Pro Cys
65                  70                  75                  80 agg aag gat gtc ctc gtg gtg acc cct tgg ctg gct ccc att gtc tgg      288
Arg Lys Asp Val Leu Val Val Thr Pro Trp Leu Ala Pro Ile Val Trp
                85                  90                  95 gag ggc acg ttc aac atc gac atc ctc aac gag cag ttc agg ctc cag      336
Glu Gly Thr Phe Asn Ile Asp Ile Leu Asn Glu Gln Phe Arg Leu Gln
                100                 105                 110 aac acc acc att ggg tta act gtg ttt gcc atc aag aaa tac gtg gct      384
Asn Thr Thr Ile Gly Leu Thr Val Phe Ala Ile Lys Lys Tyr Val Ala
            115                 120                 125
```

| | | |
|---|---|---|
| ttc ctg aag ctg ttc ctg gag acg gcg gag aag cac ttc atg gtg ggc<br>Phe Leu Lys Leu Phe Leu Glu Thr Ala Glu Lys His Phe Met Val Gly<br>130                                 135                        140 | | 432 |
| cac cgt gtc cac tac tat gtc ttc acc gac cag ccg gcc gcg gtg ccc<br>His Arg Val His Tyr Tyr Val Phe Thr Asp Gln Pro Ala Ala Val Pro<br>145                                 150                         155                        160 | | 480 |
| cgc gtg acg ctg ggg acc ggt cgg cag ctg tca gtg ctg gag gtg ggc<br>Arg Val Thr Leu Gly Thr Gly Arg Gln Leu Ser Val Leu Glu Val Gly<br>                           165                         170                         175 | | 528 |
| gcc tac aag cgc tgg cag gac gtg tcc atg cgc cgc atg gag atg atc<br>Ala Tyr Lys Arg Trp Gln Asp Val Ser Met Arg Arg Met Glu Met Ile<br>                    180                         185                        190 | | 576 |
| agt gac ttc tgc gag cgg cgc ttc ctc agc gag gtg gat tac ctg gtg<br>Ser Asp Phe Cys Glu Arg Arg Phe Leu Ser Glu Val Asp Tyr Leu Val<br>195                                 200                         205 | | 624 |
| tgc gtg gac gtg gac atg gag ttc cgc gac cat gtg ggc gtg gag atc<br>Cys Val Asp Val Asp Met Glu Phe Arg Asp His Val Gly Val Glu Ile<br>          210                         215                         220 | | 672 |
| ctg act ccg ctg ttc ggc acc ctg cac ccc agc ttc tac gga agc agc<br>Leu Thr Pro Leu Phe Gly Thr Leu His Pro Ser Phe Tyr Gly Ser Ser<br>225                                 230                         235                        240 | | 720 |
| cgg gag gcc ttc acc tac gag cgc cgg ccc cag tcc cag gcc tac atc<br>Arg Glu Ala Phe Thr Tyr Glu Arg Arg Pro Gln Ser Gln Ala Tyr Ile<br>                           245                         250                         255 | | 768 |
| ccc aag gac gag ggc gat ttc tac tac atg ggg gcg ttc ttc ggg ggg<br>Pro Lys Asp Glu Gly Asp Phe Tyr Tyr Met Gly Ala Phe Phe Gly Gly<br>                    260                         265                        270 | | 816 |
| tcg gtg caa gag gtg cag cgg ctc acc agg gcc tgc cac cag gcc atg<br>Ser Val Gln Glu Val Gln Arg Leu Thr Arg Ala Cys His Gln Ala Met<br>275                                 280                         285 | | 864 |
| atg gtc gac cag gcc aac ggc atc gag gcc gtg tgg cac gac gag agc<br>Met Val Asp Gln Ala Asn Gly Ile Glu Ala Val Trp His Asp Glu Ser<br>290                                 295                         300 | | 912 |
| cac ctg aac aag tac cta ctg cgc cac aaa ccc acc aag gtg ctc tcc<br>His Leu Asn Lys Tyr Leu Leu Arg His Lys Pro Thr Lys Val Leu Ser<br>305                                 310                         315                        320 | | 960 |
| ccc gag tac ttg tgg gac cag cag ctg ctg ggc tgg ccc gcc gtc ctg<br>Pro Glu Tyr Leu Trp Asp Gln Gln Leu Leu Gly Trp Pro Ala Val Leu<br>                           325                         330                         335 | | 1008 |
| agg aag ctg agg ttc act gcg gtg ccc aag aac cac cag gcg gtc cgg<br>Arg Lys Leu Arg Phe Thr Ala Val Pro Lys Asn His Gln Ala Val Arg<br>                    340                         345                        350 | | 1056 |
| aac ccg tga<br>Asn Pro | | 1065 |

<210> SEQ ID NO 5
<211> LENGTH: 354
<212> TYPE: PRT
<213> ORGANISM: Homo sapiens

<400> SEQUENCE: 5

Met Ala Glu Val Leu Arg Thr Leu Ala Gly Lys Pro Lys Cys His Ala
1                 5                    10                  15

Leu Arg Pro Met Ile Leu Phe Leu Ile Met Leu Val Leu Val Leu Phe
                 20                   25                    30

Gly Tyr Gly Val Leu Ser Pro Arg Ser Leu Met Pro Gly Ser Leu Glu
             35                    40                    45

Arg Gly Phe Cys Met Ala Val Arg Glu Pro Asp His Leu Gln Arg Val
     50                    55                    60

```
Ser Leu Pro Arg Met Val Tyr Pro Gln Pro Lys Val Leu Thr Pro Cys
 65                  70                  75                  80

Arg Lys Asp Val Leu Val Val Thr Pro Trp Leu Ala Pro Ile Val Trp
                 85                  90                  95

Glu Gly Thr Phe Asn Ile Asp Ile Leu Asn Glu Gln Phe Arg Leu Gln
            100                 105                 110

Asn Thr Thr Ile Gly Leu Thr Val Phe Ala Ile Lys Lys Tyr Val Ala
        115                 120                 125

Phe Leu Lys Leu Phe Leu Glu Thr Ala Glu Lys His Phe Met Val Gly
    130                 135                 140

His Arg Val His Tyr Tyr Val Phe Thr Asp Gln Pro Ala Ala Val Pro
145                 150                 155                 160

Arg Val Thr Leu Gly Thr Gly Arg Gln Leu Ser Val Leu Glu Val Gly
                165                 170                 175

Ala Tyr Lys Arg Trp Gln Asp Val Ser Met Arg Arg Met Glu Met Ile
            180                 185                 190

Ser Asp Phe Cys Glu Arg Arg Phe Leu Ser Glu Val Asp Tyr Leu Val
        195                 200                 205

Cys Val Asp Val Asp Met Glu Phe Arg Asp His Val Gly Val Glu Ile
    210                 215                 220

Leu Thr Pro Leu Phe Gly Thr Leu His Pro Ser Phe Tyr Gly Ser Ser
225                 230                 235                 240

Arg Glu Ala Phe Thr Tyr Glu Arg Arg Pro Gln Ser Gln Ala Tyr Ile
                245                 250                 255

Pro Lys Asp Glu Gly Asp Phe Tyr Tyr Met Gly Ala Phe Phe Gly Gly
            260                 265                 270

Ser Val Gln Glu Val Gln Arg Leu Thr Arg Ala Cys His Gln Ala Met
        275                 280                 285

Met Val Asp Gln Ala Asn Gly Ile Glu Ala Val Trp His Asp Glu Ser
    290                 295                 300

His Leu Asn Lys Tyr Leu Leu Arg His Lys Pro Thr Lys Val Leu Ser
305                 310                 315                 320

Pro Glu Tyr Leu Trp Asp Gln Gln Leu Leu Gly Trp Pro Ala Val Leu
                325                 330                 335

Arg Lys Leu Arg Phe Thr Ala Val Pro Lys Asn His Gln Ala Val Arg
            340                 345                 350

Asn Pro

<210> SEQ ID NO 6
<211> LENGTH: 376
<212> TYPE: PRT
<213> ORGANISM: Platyrrhinus helleri

<400> SEQUENCE: 6

Met Asn Val Lys Gly Lys Val Ile Leu Ser Met Leu Val Val Ser Thr
 1               5                  10                  15

Val Ile Val Val Phe Trp Glu Tyr Ile Asn Ser Pro Glu Gly Ser Phe
                 20                  25                  30

Leu Trp Ile Tyr His Ser Lys Asn Pro Glu Val Asp Asp Ser Ser Ala
             35                  40                  45

Gln Lys Asp Trp Trp Phe Pro Gly Trp Phe Asn Asn Gly Ile His Asn
     50                  55                  60

Tyr Gln Gln Glu Glu Glu Asp Thr Asp Lys Glu Lys Gly Arg Glu Glu
 65                  70                  75                  80
```

Glu Gln Lys Lys Glu Asp Asp Thr Thr Glu Leu Arg Leu Trp Asp Trp
                85                  90                  95

Phe Asn Pro Lys Lys Arg Pro Glu Val Met Thr Val Thr Gln Trp Lys
                100                 105                 110

Ala Pro Val Val Trp Glu Gly Thr Tyr Asn Lys Ala Ile Leu Glu Asn
                115                 120                 125

Tyr Tyr Ala Lys Gln Lys Ile Thr Val Gly Leu Thr Val Phe Ala Ile
            130                 135                 140

Gly Arg Tyr Ile Glu His Tyr Leu Glu Phe Val Thr Ser Ala Asn
145                 150                 155                 160

Arg Tyr Phe Met Val Gly His Lys Val Ile Phe Tyr Val Met Val Asp
                165                 170                 175

Asp Val Ser Lys Ala Pro Phe Ile Glu Leu Gly Pro Leu Arg Ser Phe
                180                 185                 190

Lys Val Phe Glu Val Lys Pro Glu Lys Arg Trp Gln Asp Ile Ser Met
                195                 200                 205

Met Arg Met Lys Thr Ile Gly Glu His Ile Leu Ala His Ile Gln His
                210                 215                 220

Glu Val Asp Phe Leu Phe Cys Met Asp Val Asp Gln Val Phe Gln Asp
225                 230                 235                 240

His Phe Gly Val Glu Thr Leu Gly Gln Ser Val Ala Gln Leu Gln Ala
                245                 250                 255

Trp Trp Tyr Lys Ala Asp Pro Asp Asp Phe Thr Tyr Glu Arg Arg Lys
                260                 265                 270

Glu Ser Ala Ala Tyr Ile Pro Phe Gly Gln Gly Asp Phe Tyr Tyr His
                275                 280                 285

Ala Ala Ile Phe Gly Gly Thr Pro Ile Gln Val Leu Asn Ile Thr Gln
                290                 295                 300

Glu Cys Phe Lys Gly Ile Leu Leu Asp Lys Lys Asn Asp Ile Glu Ala
305                 310                 315                 320

Glu Trp His Asp Glu Ser His Leu Asn Lys Tyr Phe Leu Leu Asn Lys
                325                 330                 335

Pro Ser Lys Ile Leu Ser Pro Glu Tyr Cys Trp Asp Tyr His Ile Gly
                340                 345                 350

Leu Pro Ser Asp Ile Lys Thr Val Lys Leu Ser Trp Gln Thr Lys Glu
                355                 360                 365

Tyr Asn Leu Val Arg Lys Asn Val
                370                 375

<210> SEQ ID NO 7
<211> LENGTH: 227
<212> TYPE: PRT
<213> ORGANISM: Homo sapiens

<400> SEQUENCE: 7

Arg Tyr Asn Asp His Tyr Leu Glu Glu Phe Ile Thr Ser Ala Asn Arg
1               5                   10                  15

Tyr Phe Met Val Gly His Lys Val Ile Phe Tyr Ile Met Val Asp Asp
                20                  25                  30

Val Ser Lys Leu Pro Phe Ile Glu Leu Gly Pro Leu His Ser Phe Lys
                35                  40                  45

Met Phe Glu Val Lys Pro Glu Lys Arg Trp Gln Asp Ile Ser Met Met
            50                  55                  60

Arg Met Lys Ile Thr Gly Glu His Ile Leu Ala His Ile Gln His Glu
65                  70                  75                  80

```
Val Asp Phe Leu Phe Cys Met Asp Val Asp Gln Val Phe Gln Asp His
            85                  90                  95

Phe Gly Val Glu Thr Leu Gly Gln Ser Val Ala Gln Leu Gln Trp Arg
            100                 105                 110

Tyr Lys Ala Asp Pro Tyr Asp Phe Thr Glu Arg Trp Lys Glu Ser Ala
            115                 120                 125

Gly Tyr Ile Pro Phe Gly Gly Asp Phe Tyr His Ala Ala Ile Ser
            130                 135                 140

Gly Gly Thr Pro Ile Gln Val Leu Asn Ile Thr Gln Glu Cys Phe Lys
145                 150                 155                 160

Gly Ile Leu Leu Asp Lys Lys Asn Asp Ile Glu Ala Lys Trp His Asp
            165                 170                 175

Glu Ser His Leu Asn Lys Tyr Phe Leu Leu Asn Lys Pro Ser Lys Ile
            180                 185                 190

Leu Ser Leu Lys Tyr Cys Trp Asp Tyr His Ile Gly Leu Pro Ser Asp
            195                 200                 205

Ile Lys Thr Val Lys Ser Trp Gln Thr Lys Glu Tyr Asn Leu Val Arg
            210                 215                 220

Asn Asn Val
225

<210> SEQ ID NO 8
<211> LENGTH: 369
<212> TYPE: PRT
<213> ORGANISM: Ovis aries

<400> SEQUENCE: 8

Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
            20                  25                  30

Phe Trp Ile Asn Pro Ser Arg Asn Pro Glu Val Ser Gly Gly Ser Ser
            35                  40                  45

Ile Gln Lys Gly Trp Trp Phe Pro Arg Trp Phe Asn Asn Gly Tyr Gln
50                  55                  60

Glu Glu Asp Glu Asp Val Asp Glu Glu Lys Gln Arg Lys Glu Asp
65                  70                  75                  80

Lys Ser Lys Leu Lys Leu Ser Asp Trp Phe Asn Pro Phe Lys Arg Pro
            85                  90                  95

Glu Val Val Thr Met Thr Asp Trp Lys Ala Pro Val Val Trp Glu Gly
            100                 105                 110

Thr Tyr Asn Arg Ala Val Leu Asp Asp Tyr Tyr Ala Lys Gln Lys Ile
            115                 120                 125

Thr Val Gly Leu Thr Val Phe Ala Val Gly Arg Tyr Ile Glu His Tyr
            130                 135                 140

Leu Glu Glu Phe Leu Thr Ser Ala Asn Lys His Phe Met Val Gly His
145                 150                 155                 160

Arg Val Ile Phe Tyr Val Met Val Asp Val Ser Arg Met Pro Leu
            165                 170                 175

Ile Glu Leu Gly Pro Leu Arg Ser Phe Lys Val Phe Glu Val Lys Pro
            180                 185                 190

Glu Arg Arg Trp Gln Asp Val Ser Met Val Arg Met Lys Thr Ile Gly
            195                 200                 205

Glu His Ile Val Ala His Ile Gln Arg Glu Val Asp Phe Leu Phe Cys
```

-continued

```
        210                 215                 220
Met Asp Val Asp Gln Val Phe Gln Asp Glu Phe Gly Val Glu Thr Leu
225                 230                 235                 240

Gly Glu Ser Val Ala Gln Leu Gln Ala Trp Trp Tyr Lys Ala Asp Pro
                245                 250                 255

Asp Glu Phe Thr Tyr Glu Arg Arg Lys Glu Ser Ala Ala Tyr Ile Pro
                260                 265                 270

Phe Gly Glu Gly Asp Phe Tyr Tyr His Ala Ala Ile Phe Gly Gly Thr
                275                 280                 285

Pro Thr Gln Val Leu Asn Ile Thr Gln Glu Cys Phe Lys Gly Ile Leu
                290                 295                 300

Lys Asp Lys Lys Asn Asp Ile Glu Ala Gln Trp His Asp Glu Ser His
305                 310                 315                 320

Leu Asn Lys Tyr Phe Leu Leu Asn Lys Pro Thr Lys Ile Leu Ser Pro
                325                 330                 335

Glu Tyr Cys Trp Asp Tyr His Ile Gly Leu Pro Ala Asp Ile Lys Leu
                340                 345                 350

Val Lys Met Ser Trp Gln Thr Lys Glu Tyr Asn Val Val Arg Asn Asn
                355                 360                 365

Val
```

<210> SEQ ID NO 9
<211> LENGTH: 368
<212> TYPE: PRT
<213> ORGANISM: Bos taurus

<400> SEQUENCE: 9

```
Met Asn Val Lys Gly Lys Val Ile Leu Ser Met Leu Val Val Ser Thr
1               5                   10                  15

Val Ile Val Val Phe Trp Glu Tyr Ile His Ser Pro Glu Gly Ser Leu
                20                  25                  30

Phe Trp Ile Asn Pro Ser Arg Asn Pro Glu Val Gly Gly Ser Ser Ile
            35                  40                  45

Gln Lys Gly Trp Trp Leu Pro Arg Trp Phe Asn Asn Gly Tyr His Glu
50                  55                  60

Glu Asp Gly Asp Ile Asn Glu Glu Lys Glu Gln Arg Asn Glu Asp Glu
65                  70                  75                  80

Ser Lys Leu Lys Leu Ser Asp Trp Phe Asn Pro Phe Lys Arg Pro Glu
                85                  90                  95

Val Val Thr Met Thr Lys Trp Lys Ala Pro Val Val Trp Glu Gly Thr
                100                 105                 110

Tyr Asn Arg Ala Val Leu Asp Asn Tyr Tyr Ala Lys Gln Lys Ile Thr
            115                 120                 125

Val Gly Leu Thr Val Phe Ala Val Gly Arg Tyr Ile Glu His Tyr Leu
        130                 135                 140

Glu Glu Phe Leu Thr Ser Ala Asn Lys His Phe Met Val Gly His Pro
145                 150                 155                 160

Val Ile Phe Tyr Ile Met Val Asp Asp Val Ser Arg Met Pro Leu Ile
                165                 170                 175

Glu Leu Gly Pro Leu Arg Ser Phe Lys Val Phe Lys Ile Lys Pro Glu
            180                 185                 190

Lys Arg Trp Gln Asp Ile Ser Met Met Arg Met Lys Thr Ile Gly Glu
        195                 200                 205

His Ile Val Ala His Ile Gln His Glu Val Asp Phe Leu Phe Cys Met
```

```
               210                 215                 220
Asp Val Asp Gln Val Phe Gln Asp Lys Phe Gly Val Glu Thr Leu Gly
225                 230                 235                 240

Glu Ser Val Ala Gln Leu Gln Ala Trp Trp Tyr Lys Ala Asp Pro Asn
                245                 250                 255

Asp Phe Thr Tyr Glu Arg Arg Lys Glu Ser Ala Ala Tyr Ile Pro Phe
                260                 265                 270

Gly Glu Gly Asp Phe Tyr Tyr His Ala Ala Ile Phe Gly Gly Thr Pro
                275                 280                 285

Thr Gln Val Leu Asn Ile Thr Gln Glu Cys Phe Lys Gly Ile Leu Lys
                290                 295                 300

Asp Lys Lys Asn Asp Ile Glu Ala Gln Trp His Asp Glu Ser His Leu
305                 310                 315                 320

Asn Lys Tyr Phe Leu Leu Asn Lys Pro Thr Lys Ile Leu Ser Pro Glu
                325                 330                 335

Tyr Cys Trp Asp Tyr His Ile Gly Leu Pro Ala Asp Ile Lys Leu Val
                340                 345                 350

Lys Met Ser Trp Gln Thr Lys Glu Tyr Asn Val Val Arg Asn Asn Val
                355                 360                 365

<210> SEQ ID NO 10
<211> LENGTH: 371
<212> TYPE: PRT
<213> ORGANISM: Sus scrofa

<400> SEQUENCE: 10

Met Asn Val Lys Gly Arg Val Val Leu Ser Met Leu Leu Val Ser Thr
1               5                   10                  15

Val Met Val Val Phe Trp Glu Tyr Ile Asn Ser Pro Glu Gly Ser Leu
                20                  25                  30

Phe Trp Ile Tyr Gln Ser Lys Asn Pro Glu Val Gly Ser Ser Ala Gln
                35                  40                  45

Arg Gly Trp Trp Phe Pro Ser Trp Phe Asn Asn Gly Thr His Ser Tyr
            50                  55                  60

His Glu Glu Glu Asp Ala Ile Gly Asn Glu Lys Glu Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
                100                 105                 110

Glu Gly Thr Tyr Asn Arg Ala Val Leu Asp Asn Tyr Tyr Ala Lys Gln
                115                 120                 125

Lys Ile Thr Val Gly Leu Thr Val Phe Ala Val Gly Arg Tyr Ile Glu
                130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                165                 170                 175

Pro Leu Ile Glu Leu Gly Pro Leu Arg Ser Phe Lys Val Phe Glu Ile
                180                 185                 190

Lys Ser Glu Lys Arg Trp Gln Asp Ile Ser Met Met Arg Met Lys Thr
                195                 200                 205

Ile Gly Glu His Ile Leu Ala His Ile Gln His Glu Val Asp Phe Leu
                210                 215                 220
```

```
Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
            245                 250                 255

His Pro Asp Glu Phe Thr Tyr Glu Arg Arg Lys Glu Ser Ala Ala Tyr
        260                 265                 270

Ile Pro Phe Gly Gln Gly Asp Phe Tyr Tyr His Ala Ala Ile Phe Gly
    275                 280                 285

Gly Thr Pro Thr Gln Val Leu Asn Ile Thr Gln Glu Cys Phe Lys Gly
290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
            325                 330                 335

Ser Pro Glu Tyr Cys Trp Asp Tyr His Ile Gly Met Ser Val Asp Ile
        340                 345                 350

Arg Ile Val Lys Ile Ala Trp Gln Lys Lys Glu Tyr Asn Leu Val Arg
    355                 360                 365

Asn Asn Ile
    370

<210> SEQ ID NO 11
<211> LENGTH: 359
<212> TYPE: PRT
<213> ORGANISM: Mus musculus

<400> SEQUENCE: 11

Met Asn Val Lys Gly Lys Val Ile Leu Leu Met Leu Ile Val Ser Thr
1               5                   10                  15

Val Val Val Phe Trp Glu Tyr Val Asn Arg Ile Pro Glu Val Gly
            20                  25                  30

Glu Asn Arg Trp Gln Lys Asp Trp Phe Pro Ser Trp Phe Lys Asn
            35                  40                  45

Gly Thr His Ser Tyr Gln Glu Asp Asn Val Glu Gly Arg Arg Glu Lys
            50                  55                  60

Gly Arg Asn Gly Asp Arg Ile Glu Glu Pro Gln Leu Trp Asp Trp Phe
65                  70                  75                  80

Asn Pro Lys Asn Arg Pro Asp Val Leu Thr Val Thr Pro Trp Lys Ala
                85                  90                  95

Pro Ile Val Trp Glu Gly Thr Tyr Asp Thr Ala Leu Leu Glu Lys Tyr
            100                 105                 110

Tyr Ala Thr Gln Lys Leu Thr Val Gly Leu Thr Val Phe Ala Val Gly
            115                 120                 125

Lys Tyr Ile Glu His Tyr Leu Glu Asp Phe Leu Glu Ser Ala Asp Met
    130                 135                 140

Tyr Phe Met Val Gly His Arg Val Ile Phe Tyr Val Met Ile Asp Asp
145                 150                 155                 160

Thr Ser Arg Met Pro Val Val His Leu Asn Pro Leu His Ser Leu Gln
                165                 170                 175

Val Phe Glu Ile Arg Ser Glu Lys Arg Trp Gln Asp Ile Ser Met Met
            180                 185                 190

Arg Met Lys Thr Ile Gly Glu His Ile Leu Ala His Ile Gln His Glu
            195                 200                 205

Val Asp Phe Leu Phe Cys Met Asp Val Asp Gln Val Phe Gln Asp Asn
    210                 215                 220
```

Phe Gly Val Glu Thr Leu Gly Gln Leu Val Ala Gln Leu Gln Ala Trp
225                 230                 235                 240

Trp Tyr Lys Ala Ser Pro Glu Lys Phe Thr Tyr Glu Arg Arg Glu Leu
            245                 250                 255

Ser Ala Ala Tyr Ile Pro Phe Gly Gly Asp Phe Tyr Tyr His Ala
            260                 265                 270

Ala Ile Phe Gly Gly Thr Pro Thr His Ile Leu Asn Leu Thr Arg Glu
            275                 280                 285

Cys Phe Lys Gly Ile Leu Gln Asp Lys Lys His Asp Ile Glu Ala Gln
            290                 295                 300

Trp His Asp Glu Ser His Leu Asn Lys Tyr Phe Leu Phe Asn Lys Pro
305                 310                 315                 320

Thr Lys Ile Leu Ser Pro Glu Tyr Cys Trp Asp Tyr Gln Ile Gly Leu
            325                 330                 335

Pro Ser Asp Ile Lys Ser Val Lys Val Ala Trp Gln Thr Lys Glu Tyr
            340                 345                 350

Asn Leu Val Arg Asn Asn Val
            355

<210> SEQ ID NO 12
<211> LENGTH: 376
<212> TYPE: PRT
<213> ORGANISM: Artificial Sequence
<220> FEATURE:
<223> OTHER INFORMATION: Consensus of mammalian galactosyl transferase
      sequences - this in vention

<400> SEQUENCE: 12

Met Asn Val Lys Gly Lys Val Ile Leu Ser Met Leu Val Val Ser Thr
1               5                   10                  15

Val Ile Val Val Phe Trp Glu Tyr Ile Asn Ser Pro Glu Gly Ser Phe
            20                  25                  30

Leu Trp Ile Tyr His Ser Lys Asn Pro Glu Val Asp Asp Ser Ser Ala
        35                  40                  45

Gln Lys Asp Trp Trp Phe Pro Gly Trp Phe Asn Asn Gly Ile His Asn
50                  55                  60

Tyr Gln Gln Glu Glu Glu Asp Thr Asp Lys Lys Gly Arg Glu Glu
65                  70                  75                  80

Glu Gln Lys Lys Glu Asp Asp Thr Thr Glu Leu Arg Leu Trp Asp Trp
            85                  90                  95

Phe Asn Pro Lys Lys Arg Pro Glu Val Met Thr Val Thr Gln Trp Lys
            100                 105                 110

Ala Pro Val Val Trp Glu Gly Thr Tyr Asn Lys Ala Ile Leu Glu Asn
            115                 120                 125

Tyr Tyr Ala Lys Gln Lys Ile Thr Val Gly Leu Thr Val Phe Ala Ile
        130                 135                 140

Gly Arg Tyr Ile Glu His Tyr Leu Glu Glu Phe Leu Thr Ser Ala Asn
145                 150                 155                 160

Arg Tyr Phe Met Val Gly His Lys Val Ile Phe Tyr Val Met Val Asp
            165                 170                 175

Asp Val Ser Lys Ala Pro Phe Ile Glu Leu Gly Pro Leu Arg Ser Phe
            180                 185                 190

Lys Val Phe Glu Val Lys Pro Glu Lys Arg Trp Gln Asp Ile Ser Met
        195                 200                 205

Met Arg Met Lys Thr Ile Gly Glu His Ile Leu Ala His Ile Gln His

-continued

```
            210                 215                 220
Glu Val Asp Phe Leu Phe Cys Met Asp Val Asp Gln Val Phe Gln Asp
225                 230                 235                 240

His Phe Gly Val Glu Thr Leu Gly Gln Ser Val Ala Gln Leu Gln Ala
                245                 250                 255

Trp Trp Tyr Lys Ala Asp Pro Asp Phe Thr Tyr Glu Arg Arg Lys
                260                 265                 270

Glu Ser Ala Ala Tyr Ile Pro Phe Gly Gln Gly Asp Phe Tyr His
            275                 280                 285

Ala Ala Ile Phe Gly Gly Thr Pro Ile Gln Val Leu Asn Ile Thr Gln
        290                 295                 300

Glu Cys Phe Lys Gly Ile Leu Leu Asp Lys Lys Asn Asp Ile Glu Ala
305                 310                 315                 320

Glu Trp His Asp Glu Ser His Leu Asn Lys Tyr Phe Leu Leu Asn Lys
                325                 330                 335

Pro Ser Lys Ile Leu Ser Pro Glu Tyr Cys Trp Asp Tyr His Ile Gly
                340                 345                 350

Leu Pro Ser Asp Ile Lys Thr Val Lys Leu Ser Trp Gln Thr Lys Glu
            355                 360                 365

Tyr Asn Leu Val Arg Lys Asn Val
        370                 375

<210> SEQ ID NO 13
<211> LENGTH: 376
<212> TYPE: PRT
<213> ORGANISM: Artificial Sequence
<220> FEATURE:
<223> OTHER INFORMATION: Humanized galactosyl transferase sequence -
      This invention

<400> SEQUENCE: 13

Met Asn Val Lys Gly Lys Val Ile Leu Ser Met Leu Val Val Ser Thr
1               5                   10                  15

Val Ile Val Val Phe Trp Glu Tyr Ile Asn Ser Pro Glu Gly Ser Phe
            20                  25                  30

Leu Trp Ile Tyr His Ser Lys Asn Pro Glu Val Asp Asp Ser Ser Ala
        35                  40                  45

Gln Lys Asp Trp Trp Phe Pro Gly Trp Phe Asn Asn Gly Ile His Asn
50                  55                  60

Tyr Gln Gln Glu Glu Asp Thr Asp Lys Glu Lys Gly Arg Glu Glu
65                  70                  75                  80

Glu Gln Lys Lys Glu Asp Asp Thr Thr Glu Leu Arg Leu Trp Asp Trp
                85                  90                  95

Phe Asn Pro Lys Lys Arg Pro Glu Val Met Thr Val Thr Gln Trp Lys
            100                 105                 110

Ala Pro Val Val Trp Glu Gly Thr Tyr Asn Lys Ala Ile Leu Glu Asn
        115                 120                 125

Tyr Tyr Ala Lys Gln Lys Ile Thr Val Gly Leu Thr Val Phe Ala Ile
    130                 135                 140

Gly Arg Tyr Ile Asp His Tyr Leu Glu Glu Phe Leu Thr Ser Ala Asn
145                 150                 155                 160

Arg Tyr Phe Met Val Gly His Lys Val Ile Phe Tyr Ile Met Val Asp
                165                 170                 175

Asp Val Ser Lys Ala Pro Phe Ile Glu Leu Gly Pro Leu Arg Ser Phe
            180                 185                 190
```

-continued

```
Lys Val Phe Glu Val Lys Pro Glu Lys Arg Trp Gln Asp Ile Ser Met
        195                 200                 205

Met Arg Met Lys Ile Thr Gly Glu His Ile Leu Ala His Ile Gln His
    210                 215                 220

Glu Val Asp Phe Leu Phe Cys Met Asp Val Asp Gln Val Phe Gln Asp
225                 230                 235                 240

His Phe Gly Val Glu Thr Leu Gly Gln Ser Val Ala Gln Leu Gln Ala
                245                 250                 255

Trp Trp Tyr Lys Ala Asp Pro Asp Phe Thr Tyr Glu Arg Arg Lys
        260                 265                 270

Glu Ser Ala Gly Tyr Ile Pro Phe Gly Gln Gly Asp Phe Tyr His
    275                 280                 285

Ala Ala Ile Phe Gly Gly Thr Pro Ile Gln Val Leu Asn Ile Thr Gln
    290                 295                 300

Glu Cys Phe Lys Gly Ile Leu Leu Asp Lys Lys Asn Asp Ile Glu Ala
305                 310                 315                 320

Glu Trp His Asp Glu Ser His Leu Asn Lys Tyr Phe Leu Leu Asn Lys
                325                 330                 335

Pro Ser Lys Ile Leu Ser Pro Glu Tyr Cys Trp Asp Tyr His Ile Gly
        340                 345                 350

Leu Pro Ser Asp Ile Lys Thr Val Lys Leu Ser Trp Gln Thr Lys Glu
        355                 360                 365

Tyr Asn Leu Val Arg Lys Asn Val
        370                 375

<210> SEQ ID NO 14
<211> LENGTH: 1131
<212> TYPE: DNA
<213> ORGANISM: Platyrrhinus helleri

<400> SEQUENCE: 14
atgaatgtca aaggaaaagt aattctgtcg atgctggttg tctcaactgt gattgttgtg      60
ttttgggaat atatcaacag cccagaaggc tctttcttgt ggatatatca ctcaaagaac     120
ccagaagttg atgacagcag tgctcagaag gactggtggt ttcctggctg gtttaacaat     180
gggatccaca attatcaaca agaggaagaa gacacagaca agaaaaaagg aagagaggag     240
gaacaaaaaa aggaagatga cacaacagag cttcggctat gggactggtt taatccaaag     300
aaacgcccag aggttatgac agtgacccaa tggaaggcgc cggttgtgtg ggaaggcact     360
tacaacaaag ccatcctaga aaattattat gccaaacaga aaattaccgt ggggttgacg     420
gttttttgcta ttggaagata tattgagcat tacttggagg agttcgtaac atctgctaat     480
aggtacttca tggtcggcca caaagtcata ttttatgtca tggtggatga tgtctccaag     540
gcgccgttta tagagctggg tcctctgcgt tccttcaaag tgtttgaggt caagccagag     600
aagaggtggc aagacatcag catgatgcgt atgaagacca tcggggagca catcttggcc     660
cacatccaac acgaggttga cttcctcttc tgcatggatg tggaccaggt cttccaagac     720
cattttgggg tagagaccct gggccagtcg gtggctcagc tacaggcctg gtggtacaag     780
gcagatcctg atgactttac ctatgagagg cggaaagagt cggcagcata tattccattt     840
ggccagggg gatttttatta ccatgcagcc atttttggag aacaccgat tcaggttctc     900
aacatcaccc aggagtgctt taagggaatc ctcctggaca agaaaaatga catagaagcc     960
gagtggcatg atgaaagcca cctaaacaag tatttccttc tcaacaaacc ctctaaaatc    1020
ttatctccag aatactgctg ggattatcat ataggcctgc cttcagatat taaaactgtc    1080
```
aagctatcat ggcaaacaaa agagtataat ttggttagaa agaatgtctg a      1131

<210> SEQ ID NO 15
<211> LENGTH: 755
<212> TYPE: DNA
<213> ORGANISM: Homo sapiens

<400> SEQUENCE: 15
cagcttgtgg tttctttcag gaatcccaga ggataaatgt tttgcttttc ttctttgttt      60
cagatataat gatcattact tggaggagtt cataacatct gctaataggt acttcatggt     120
tggccacaaa gtcatatttt acatcatggt ggatgatgtc tccaagctgc cgtttataga     180
gctgggtcct ctgcattcct tcaaaatgtt tgaggtcaag ccagagaaga ggtggcaaga     240
catcagcatg atgcgtatga agatcactgg ggagcacatc ttggcccaca tccaacacga     300
ggtcgacttc ctcttctgca tggatgtgga ccaggtcttc aagaccatt tggggtgga      360
gaccctaggc cagtcagtgg ctcagctaca ggctggcggt acaaggcaga tccctatgac     420
tttacctagg agaggtggaa agagtcagca ggatacattc catttggcca ggggattttt     480
attaccatgc agccatttct ggaggaacac ccattcaggt tctcaacatc acccaggagt     540
gctttaaggg aatcctcctg gacaagaaaa atgacataga agccaagtgg catgatgaaa     600
gccacctaaa caagtatttc cttctcaata aaccctctaa aatcttatcc ctaaaatact     660
gctgggatta tcataggc ctgccttcag atattaaaac tgtcaagtga tcgtggcaga      720
caaaagagta aatttggtt agaaataatg tctga                                755

<210> SEQ ID NO 16
<211> LENGTH: 1131
<212> TYPE: DNA
<213> ORGANISM: Artificial Sequence
<220> FEATURE:
<223> OTHER INFORMATION: Humanized galactosyl transferase sequence -
      This invention

<400> SEQUENCE: 16
atgaatgtca aggaaaagt aattctgtcg atgctggttg tctcaactgt gattgttgtg      60
ttttgggaat atatcaacag cccagaaggc tctttcttgt ggatatatca ctcaaagaac     120
ccagaagttg atgacagcag tgctcagaag gactggtggt ttcctggctg gtttaacaat     180
gggatccaca attatcaaca agaggaagaa gacacagaca agaaaaagg aagagaggag     240
gaacaaaaaa aggaagatga cacaacagag cttcggctat gggactggtt taatccaaag     300
aaacgcccag aggttatgac agtgacccaa tggaaggcgc cggttgtgtg ggaaggcact     360
tacaacaaag ccatcctaga aaattattat gccaaacaga aaattaccgt ggggttgacg     420
gttttttgcta ttggaagata tattgatcat tacttggagg agttcttaac atctgctaat     480
aggtacttca tggttggcca caaagtcata ttttacatca tggtggatga tgtctccaag     540
gcgccgttta tagagctggg tcctctgcgt tccttcaaag tgtttgaggt caagccagag     600
aagaggtggc aagacatcag catgatgcgt atgaagatca ctggggagca catcttggcc     660
cacatccaac acgaggtcga cttcctcttc tgcatggatg tggaccaggt cttccaagac     720
cattttgggg tggagaccct aggccagtca gtggctcagc tacaggcctg gtggtacaag     780
gcagatcccg atgactttac ctatgagagg cggaaagagt cagcaggata cattccattt     840
ggccaggggg attttattta ccatgcagcc attttggag gaacacccat tcaggttctc     900
aacatcaccc aggagtgctt taagggaatc ctcctggaca gaaaatga catagaagcc     960

```
gagtggcatg atgaaagcca cctaaacaag tatttccttc tcaataaacc ctctaaaatc    1020
ttatccccag aatactgctg ggattatcat ataggcctgc cttcagatat taaaactgtc    1080
aagctatcgt ggcagacaaa agagtataat ttggttagaa ataatgtctg a             1131

<210> SEQ ID NO 17
<211> LENGTH: 1303
<212> TYPE: DNA
<213> ORGANISM: Ovis aries

<400> SEQUENCE: 17
agccgaggac gccgccgggg agccgaggct ccggccagcc cccagcgcgc ccagcttctg      60
cagatcagga gtcagaacgc tgcaccttcg cttcctccca gccctgcctc cttctgcaaa    120
acggagctca atagaacttg gtacttttgc cttttactct gggaggagag aagcagacga    180
tgaggagaaa ataatgaatg tcaaaggaaa agtgattctg tcaatgctgg ttgtctcaac    240
tgtcattgtt gtgttttggg aatatatcca cagcccagaa ggctctttgt tctggataaa    300
cccatcaaga aacccagaag tcagtggcgg cagcagcatt cagaagggct ggtggtttcc    360
gagatggttt aacaatggtt accaagaaga agatgaagac gtagacgaag aaaaggaaca    420
aagaaaggaa gacaaaagca agcttaagct atcggactgg ttcaacccat ttaaacgccc    480
tgaggttgtg actatgacag attggaaggc acccgtggtg tgggaaggca cttacaacag    540
agccgtctta gacgattact acgccaagca gaaaattacc gtcggcctga cggttttcgc    600
cgtcggaaga tacattgagc attacttgga ggagttctta acgtctgcta ataagcactt    660
catggttggc caccgagtca tcttttacgt catggtggac gacgtctcca ggatgccttt    720
gatagagctg ggccctctgc gctccttcaa agtgtttgag gtcaagcctg agaggaggtg    780
gcaggacgtc agcatggtgc gcatgaagac catcggggag cacatcgtgg cccacatcca    840
gcgtgaggtt gacttcctct tctgcatgga cgtggaccag gtcttccaag acgagttcgg    900
ggtggagacc ctgggtgagt cggtggccca gctacaggcc tggtggtaca aggcagatcc    960
cgatgagttt acctacgaga ggcgcaagga gtctgcagca tacattccct tcggcgaagg   1020
ggatttttat taccacgcag ccattttttgg gggaacaccc actcaggtcc ttaacatcac   1080
ccaggaatgc ttcaaaggaa tcctcaagga caagaaaaat gacatagaag cccaatggca   1140
tgatgagagc catctaaaca agtatttcct tctcaacaaa cccactaaaa tcttatcccc   1200
ggaatactgc tgggattatc atataggcct acctgcggat attaagcttg tcaagatgtc   1260
ttggcagaca aaagagtata atgtggttag aaataacgtc tga                     1303
```